US010634673B2

(12) United States Patent
Araz et al.

(10) Patent No.: US 10,634,673 B2
(45) Date of Patent: Apr. 28, 2020

(54) ELECTROPHORETIC BAR CODE ASSAY DEVICES AND METHODS FOR MAKING AND USING THE SAME

(71) Applicant: The Regents of the University of California, Oakland, CA (US)

(72) Inventors: M. Kursad Araz, El Cerrito, CA (US); Akwasi A. Apori, Berkeley, CA (US); Amy E. Herr, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/440,852

(22) PCT Filed: Nov. 11, 2013

(86) PCT No.: PCT/US2013/069500
§ 371 (c)(1),
(2) Date: May 5, 2015

(87) PCT Pub. No.: WO2014/075016
PCT Pub. Date: May 15, 2014

(65) Prior Publication Data
US 2015/0293089 A1    Oct. 15, 2015

Related U.S. Application Data

(60) Provisional application No. 61/783,942, filed on Mar. 14, 2013, provisional application No. 61/725,403, filed on Nov. 12, 2012.

(51) Int. Cl.
| | | |
|---|---|---|
| *G01N 33/559* | (2006.01) | |
| *B01L 3/00* | (2006.01) | |
| *G01N 33/558* | (2006.01) | |
| *G01N 33/543* | (2006.01) | |
| *G01N 27/447* | (2006.01) | |

(52) U.S. Cl.
CPC .......... *G01N 33/559* (2013.01); *B01L 3/5027* (2013.01); *G01N 27/447* (2013.01); *G01N 33/54366* (2013.01); *G01N 33/558* (2013.01); *B01L 3/502707* (2013.01); *B01L 2300/0636* (2013.01); *B01L 2300/087* (2013.01); *B01L 2300/0825* (2013.01); *B01L 2400/0415* (2013.01); *B01L 2400/0421* (2013.01); *B01L 2400/0487* (2013.01); *G01N 2333/186* (2013.01)

(58) Field of Classification Search
None
See application file for complete search history.

(56) References Cited

U.S. PATENT DOCUMENTS

| | | | |
|---|---|---|---|
| 5,356,782 A * | 10/1994 | Moorman | G01N 33/54366 422/565 |
| 7,323,143 B2 | 1/2008 | Anderson et al. | |
| 7,828,949 B2 * | 11/2010 | Jung | A61B 5/0002 204/451 |
| 7,846,676 B2 | 12/2010 | Yang et al. | |
| 7,858,396 B2 | 12/2010 | Corstjens et al. | |
| 7,939,342 B2 | 5/2011 | Song et al. | |
| 9,110,057 B2 | 8/2015 | Herr et al. | |
| 9,400,277 B2 | 7/2016 | Yang et al. | |
| 2003/0190608 A1 | 10/2003 | Blackburn | |
| 2004/0115679 A1 | 6/2004 | Tanioka et al. | |
| 2005/0106740 A1 | 5/2005 | Boyes et al. | |
| 2011/0028669 A1 | 2/2011 | Robotti et al. | |
| 2012/1035541 | 5/2011 | Song et al. | |
| 2011/0177618 A1 * | 7/2011 | Herr | B01L 3/502761 436/515 |
| 2012/0135541 A1 | 5/2012 | Herr et al. | |
| 2012/0142904 A1 | 6/2012 | He et al. | |
| 2012/0329040 A1 * | 12/2012 | Herr | B01L 3/5023 435/5 |

FOREIGN PATENT DOCUMENTS

| | | |
|---|---|---|
| CN | 102680690 | 2/2015 |
| JP | 2002243741 | 9/2002 |
| WO | 2010135364 | 2/2011 |

OTHER PUBLICATIONS

Peluso, Paul, et al. "Optimizing antibody immobilization strategies for the construction of protein microarrays." Analytical biochemistry 312.2 (2003): 113-124. (Year: 2003).*
Araz et al. (2013) "Micofluidic barcode assay for antibody-based confirmatory diagnostics," 13(19) 3910-3920.

* cited by examiner

*Primary Examiner* — Tracy Vivlemore
*Assistant Examiner* — Sahana S Kaup
(74) *Attorney, Agent, or Firm* — Rudy J. Ng; Bret Field; Bozicevic, Field & Francis LLP

(57) ABSTRACT

A microfluidic device for determining whether an analyte is present in a sample is provided. The microfluidic device includes an elongated flow path having a polymeric medium, where the polymeric medium includes a first analyte detection domain having a first immobilized capture member that specifically binds to a first analyte and a second analyte detection domain having a second immobilized capture member that specifically binds to a second analyte. Also provided are methods, systems and kits in which the subject microfluidic devices find use, as well as methods of producing the same.

31 Claims, 10 Drawing Sheets

ELECTROPHORETIC BAR CODE ASSAY DEVICES AND METHODS FOR MAKING AND USING THE SAME

CROSS-REFERENCE TO RELATED APPLICATIONS

Pursuant to 35 U.S.C. § 119 (e), this application claims priority to the filing date of U.S. Provisional Patent Application No. 61/725,403, filed Nov. 12, 2012, and U.S. Provisional Application No. 61/783,942, filed Mar. 14, 2013, the disclosures of each of which are incorporated herein by reference.

INTRODUCTION

Confirmatory diagnostic assays are useful for eliminating false positive screening results. For example, in HCV or HIV diagnosis, the U.S. Center for Disease Control and Prevention (CDC) recommends a screening enzyme immunoassay, such as an enzyme-linked immunosorbent assay (ELISA), with subsequent confirmation of a positive result using a Western blot or immunoblot. To provide higher clinical sensitivity and specificity than rapid screening assays, confirmatory blots assay multiple biomarkers in a single sample. However, even in developed nations, lack of funding is cited by public health centers as a factor that may limit access to HCV diagnostics. When considering less developed nations, the access to confirmatory diagnostics is even more limited. Accessibility limitations of confirmatory blotting assays may be due, in part, to the high resource consumption generally associated with these types of assays. In conventional formats, the assays are slow, labor intensive, and costly, which requires laboratory infrastructure and trained staff. For example, confirmatory diagnostics are presently relegated to centralized laboratories owing to laborious, multistage protocols. The capability to perform point-of-care confirmation of the presence of specific biomarkers would positively impact treatment efficacy for infectious diseases, such as hepatitis C (HCV) and HIV.

SUMMARY

A microfluidic device for determining whether an analyte is present in a sample is provided. The microfluidic device includes an elongated flow path having a polymeric medium, where the polymeric medium includes a first analyte detection domain having a first immobilized capture member that specifically binds to a first analyte and a second analyte detection domain having a second immobilized capture member that specifically binds to a second analyte. Also provided are methods, systems and kits in which the subject microfluidic devices find use, as well as methods of producing the same.

Aspects of the present disclosure include a microfluidic device. The microfluidic device includes an elongated flow path that includes a polymeric medium, where the polymeric medium includes a first analyte detection domain having a first immobilized capture member that specifically binds to a first analyte and a second analyte detection domain having a second immobilized capture member that specifically binds to a second analyte.

In some embodiments, the polymeric medium includes a polymeric gel.

In some embodiments, the first immobilized capture member is non-covalently bound to the polymeric medium in the first analyte detection domain. In some embodiments, the first immobilized capture member is non-covalent bound to the polymeric medium in the first analyte detection domain via a specific binding member pair. In some embodiments, the specific binding member pair includes biotin and streptavidin. In some embodiments, the first immobilized capture member includes streptavidin bound to the polymeric medium and biotin bound to a ligand of the first analyte.

In some embodiments, the second immobilized capture member is non-covalently bound to the polymeric medium in the second analyte detection domain. In some embodiments, the second immobilized capture member is non-covalent bound to the polymeric medium in the second analyte detection domain via a specific binding member pair. In some embodiments, the specific binding member pair includes biotin and streptavidin. In some embodiments, the second immobilized capture member includes streptavidin bound to the polymeric medium and biotin bound to a ligand of the second analyte.

Aspects of the present disclosure include a method of determining whether an analyte is present in a sample. The method includes introducing a sample into an elongated flow path that includes a polymeric medium, where the polymeric medium includes a first analyte detection domain having a first immobilized capture member that specifically binds to a first analyte and a second analyte detection domain having a second immobilized capture member that specifically binds to a second analyte. The method further includes applying a directional electric field to the elongated flow path in a manner sufficient to move components through the polymeric medium, and obtaining a signal from the first analyte detection domain and the second analyte detection domain to determine whether the first analyte and the second analyte are present in the sample.

In some embodiments, the method includes labeling the sample prior to introducing the sample into the elongated flow path.

In some embodiments, the method includes introducing a label into the elongated flow path after the sample is introduced into the elongated flow path. In some embodiments, the label includes an antibody that specifically binds to an analyte. In some embodiments, the label includes a fluorescent moiety.

In some embodiments, the analyte includes an antibody.

In some embodiments, the sample is a biological sample. In some embodiments, the sample includes blood, a blood product, urine, or saliva.

Aspects of the present disclosure include a system for assaying a fluid sample for the presence of two or more analytes. The system includes a microfluidic device according to embodiments of the present disclosure and a detector.

In some embodiments, the system further includes microfluidic components configured to direct a fluid through the microfluidic device.

Aspects of the present disclosure include a kit that includes a microfluidic device according to embodiments of the present disclosure and a packaging configured to contain the microfluidic device.

Aspects of the present disclosure include a method of producing microfluidic assay device. The method includes producing a precursor polymeric medium in an elongated flow path, where the precursor polymeric medium includes first member of a specific binding pair. The method also includes introducing into the elongated flow path a defined amount of a first capture member having a first antigen bound to a second member of the specific binding pair in a manner sufficient to produce a first analyte detection domain that includes a first immobilized capture member that specifically binds to a first analyte in the elongated flow path. The method also includes introducing into the elongated flow path a defined amount of the second member of the specific binding pair in a manner sufficient to produce a spacer domain, and introducing into the elongated flow path a defined amount of a second capture member having a second antigen bound to the second member of the specific binding pair in a manner sufficient to produce a second analyte detection domain that includes a second immobilized capture member that specifically binds to a second analyte in the elongated flow path, to produce a microfluidic assay device.

BRIEF DESCRIPTION OF THE FIGURES

FIG. 2(A) shows an image of a 17.5 mm×17.5 mm glass chip with six simple straight (2.5 mm long) microchannels, each housing a streptavidin-PA gel. FIG. 2(B) shows a fluorescence micrograph of four c100p-AF488 antigen bands and interlaced biotin spacers. FIG. 2(C) shows a schematic of an electrophoretic patterning process, which includes: (steps 1-3) Biotin blocking to create an entry area spacer via electrophoretic load, incubation, and reversed polarity field to remove unbound biotin; and (steps 4-6) Patterning of biotinylated antigen after spacer region via electrophoretic introduction, 1 minute incubation, and reversed polarity electrophoretic removal of unbound biotinylated antigen. Steps 1-6 were repeated for each subsequent reagent-spacer pair pattern.

FIG. 4(A) shows time lapse fluorescence micrographs (10 s/frame) of a patterning process for biotinylated c100p antigen (AF-488 labelled). Region (i) was previously blocked with biotin (spacer). Region (ii) was the region being patterned with the biotinylated c100p. At t=140 s, the electric field was removed and incubation was started. After a reverse polarity electrophoretic wash, Region ii had been patterned with the c100p and the open streptavidin-PA gel sites in Region iii were available for subsequent patterning with biotin spacer or biotinylated antigen. FIG. 4(B) shows a graph of the patterning process as viewed through breakthrough isotherms of axial fluorescence intensity (biotinylated c100p, AF-488 labelled); the first 11 curves at 5 s increments from t=0. FIG. 4(C) shows fluorescence micrographs showing antigen immobilization at various Da numbers. The fluorescence intensity plot of the moving boundary and first derivative are shown below the fluorescence micrographs in FIG. 4(C). FIG. 4(D) shows a graph of the width (4σ) of the moving boundary for patterning at various Da numbers.

FIG. 6(a) shows images showing that HCV c100p was immobilized in 3 distinct channels and HCV NS3, c100p and Core human antibodies (AF568 labelled) (6.65 nM, 1 ug/ml) were injected. Only c100p antibodies were captured and produced signal. FIG. 6(b) shows a cross-reactivity matrix for three HCV antibody antigen pairs. The Core antigen showed some nonspecific capture as expected, whereas NS3 and c100p pairs did not exhibit any cross-reactivity. FIG. 6(c) shows images and graphs showing that NS3 and c100p antigens were immobilized in the same channel respectively. NS3 antibody injected into the channel went through the c100p antigen region without capture and was captured only in NS3 region. C100p antibody injected to the same channel was captured in the c100p region. FIG. 6(d) shows images and graphs similar to FIG. 6(c) with the order of immobilized antigens and antibody injection order reversed, where no c100p antibody capture was observed at the NS3 antigen region. Each antibody was captured in their corresponding antigen region, regardless of the order of immobilization.

FIG. 7(A) shows fluorescence micrographs of antibody introduction into 12 different barcode assays—operated under a range of Da numbers—which show that detection was dependent on Da number. Solutions of AF-568 labelled c100p antibodies (13.5 nM) were electrophoresed into channels housing immobilized biotinylated c100p antigen using a range of voltages (10-450V, 10 min). FIG. 7(B) shows a graph of the endpoint fluorescence readout from the labelled antibody for assays in FIG. 7(A). FIG. 7(C) shows a dose response curve for the unlabelled HCV-c100p human antibodies spiked in 2% human serum. Sandwich detection was performed using AF-568 labelled goat antihuman antibodies. The lower limit of detection was 25 ng/ml or 165 pM with SNR=10.

FIG. 8 (bottom) shows the antibody capture profile of two distinct channels immobilized under the two specified loading conditions. In both channels, antibody loading parameters were the same (25V) and capture only occurred in the antigen immobilized region (ii), confirming region (iii) remained antigen free in all cases. Similar to the immobilized antigen distribution, a smoother boundary with increased transverse signal variation at the boundary was observed in the antibody signal in the channel where the antigen immobilization was performed at 1180 V/cm.

FIG. 10 (top) shows the Protein L, HCV-c100p and HIV-p24 antigen distribution in Channel 1. Channel 1 was assayed against the 2% serum sample spiked with 2 µg/ml (13.5 nM) HCV-c100p human and HVI-24p mouse antibodies. A similarly patterned Channel 2 was assayed against non-immune 2% serum as a control. Detection was performed using a cocktail of AF-568 labelled antihuman anti-mouse antibodies. Protein L regions exhibited saturated signal in both channels which confirmed the capture of highly available IgG's in the serum, validating the assay success. HCV-c100p and HIV-24 antibodies produced high signal in Channel 1 as shown in the fluorescence intensity profiles. Exposure time for the antibody micrographs was 100 ms.

DETAILED DESCRIPTION

Figure 1:
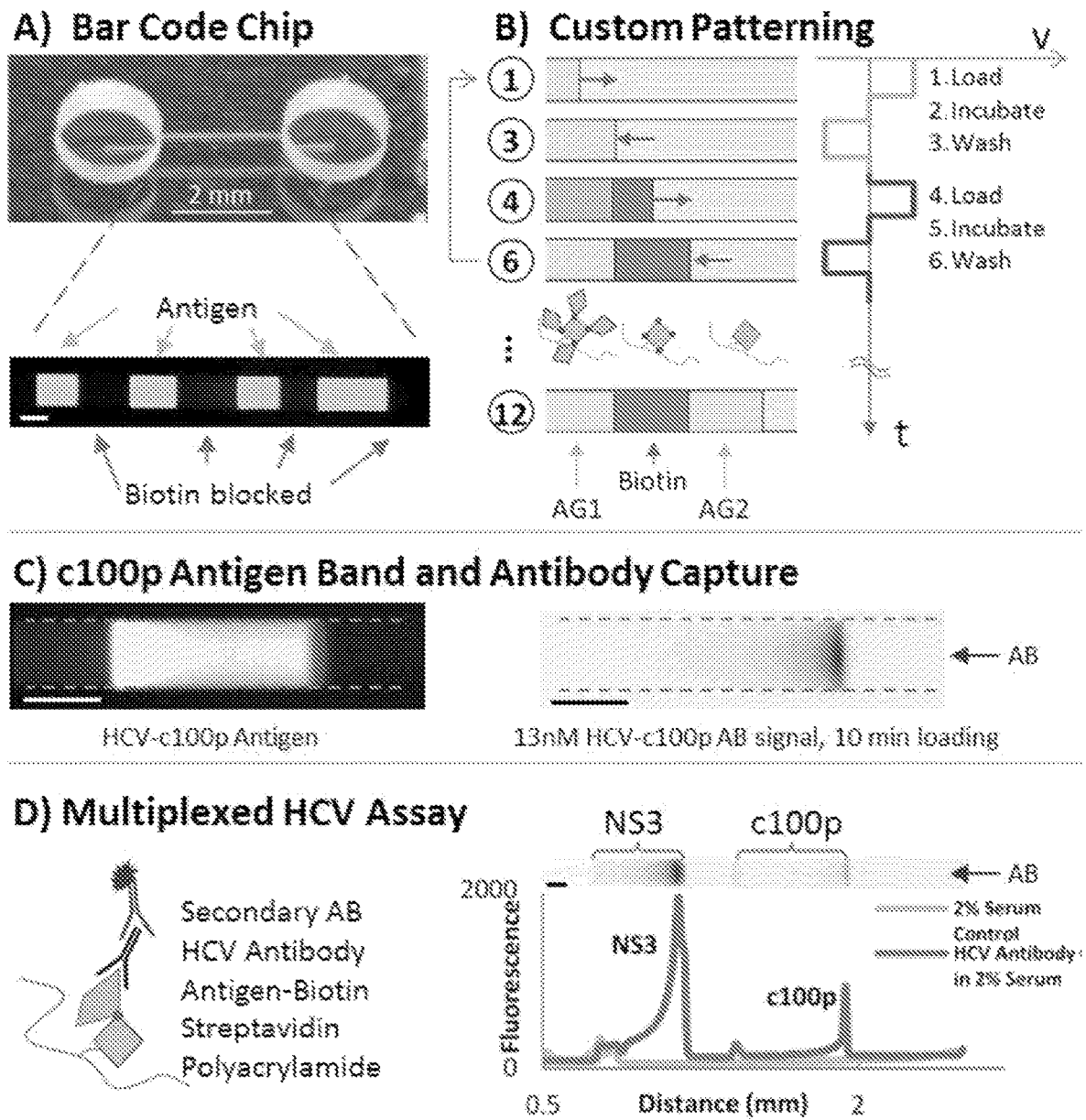
FIG. 1(a) shows an image of a microchannel in a glass chip and 4 antigen bands (biotin and AF-488 labeled c100p) with biotin blocked spacers in a channel, according to embodiments of the present disclosure.
FIG. 1(b) shows details of the patterning steps: (1) injection and immobilization; (2) incubation; (3) reverse wash of excess material; (4) repeat above steps for the next agent (e.g., biotin).
FIG. 1(c) shows an image of c100p antigen and antibody signal (10 minute assay, 2 µg/ml, 13 nM HCV-c100p human AB).
FIG. 1(d) shows a schematic and graph of the assay result of HCV-human AB (2 µg/ml, 13 nM in 2% serum) captured by NS3 and c100p antigens. Detection was performed with AF-568 labeled secondary antibodies (5 min loading and 5 min washing). The graph compares the 2 µg/ml HCV AB signal with 2% healthy serum signal (negative control). The total multistage assay time was 30 minutes. Scale bars are 100 µm long except in chip image in FIG. 1(a).

A microfluidic device for determining whether an analyte is present in a sample is provided. The microfluidic device includes an elongated flow path having a polymeric medium, where the polymeric medium includes a first analyte detection domain having a first immobilized capture member that specifically binds to a first analyte and a second analyte detection domain having a second immobilized capture member that specifically binds to a second analyte. Also provided are methods, systems and kits in which the subject microfluidic devices find use, as well as methods of producing the same.

Below, the subject microfluidic devices are described first in greater detail. Methods of detecting an analyte in a fluid sample are also disclosed in which the subject microfluidic devices find use. In addition, systems and kits that include the subject microfluidic devices are also described.

Microfluidic Devices

Embodiments of the present disclosure include microfluidic devices. In certain embodiments, the microfluidic device is configured for determining whether an analyte is present in a sample. A "microfluidic device" is a device that is configured to control and manipulate fluids geometrically constrained to a small scale (e.g., sub-millimeter). Embodiments of the microfluidic device include an elongated flow path and a polymeric medium in the elongated flow path. The polymeric medium includes a first analyte detection domain having a first immobilized capture member that specifically binds to a first analyte and a second analyte detection domain having a second immobilized capture member that specifically binds to a second analyte. One or more of the specifically bound analytes may then be detected. Additional details about the polymeric medium are discussed below.

Polymeric Medium

In certain embodiments, the microfluidic device includes a polymeric medium. The polymeric medium may include one or more analyte detection domains each having a corresponding immobilized analyte capture member that specifically binds to an analyte of interest in a sample. For example, the polymeric medium may include a first analyte detection domain having a first immobilized analyte capture member that specifically binds to a first analyte, and a second analyte detection domain having a second immobilized analyte capture member that specifically binds to a second analyte. Additional analyte detection domains and capture members may be included as desired.

The polymeric medium may be configured to have separate regions or bands for each analyte capture member. By "band" is meant a distinct detectable region where the concentration of a constituent is significantly higher than the surrounding regions. Each band of analyte capture member may include a single type of analyte capture member.

In certain embodiments, the polymeric medium is configured to bind to one or more constituents in a sample as the sample traverses the polymeric medium. In some cases, an analyte capture member of the polymeric medium is configured to specifically bind to a constituent in the sample as the sample flows through the polymeric medium as described above. Aspects of the polymeric medium include that the polymeric medium has a directional axis. In some instances, the directional axis is oriented in the direction the sample travels as the sample traverses the polymeric medium. In some embodiments, the directional axis of the polymeric medium is aligned with the length of the polymeric medium. In these embodiments, the sample traverses the polymeric medium along the length of the polymeric medium. In some cases, the length of the polymeric medium is greater than the width of the polymeric medium, such as 2 times, 3 times, 4 times, 5 times, 10 times, 25 times, 50 times, 75 times, 100 times, 125 times, 150 times, 175 times, or 200 times or more the width of the polymeric medium.

In some instances, the polymeric medium is defined by a region of the microfluidic device that includes the polymeric medium. For example, the microfluidic device may include an elongated flow path as described above. The elongated flow path may include the polymeric medium. For instance, the microfluidic device may include a channel (e.g., a microfluidic channel or capillary channel). The channel may include the polymeric medium. The polymeric medium may be included in the channel, such that a sample traverses the polymeric medium as the sample flows through the channel. In some instances, the length of the elongated flow path is greater than the width of the elongated flow path, such as 2 times, 3 times, 4 times, 5 times, 10 times, 25 times, 50 times, 75 times, 100 times, 125 times, 150 times, 175 times, or 200 or more times the width of the elongated flow path.

In certain embodiments, the polymeric medium includes a polymer, such as a polymeric gel. The polymeric gel may be a gel suitable for gel electrophoresis. The polymeric gel may include, but is not limited to, a polyacrylamide gel (e.g., methacrylamide gel), an agarose gel, and the like. The polymeric medium may be characterized based on various factors, such as, but not limited to, pore size, total polymer content (e.g., total acrylamide content), concentration of cross-linker, and the like. For instance, the polymeric medium may have a pore size that depends on the total polymer content of the polymeric medium and/or the concentration of cross-linker in the polymeric medium. In some cases, the polymeric medium may include a polyacrylamide gel that has a total acrylamide content, T (T=total concentration of acrylamide and bisacrylamide monomer), ranging from 1% to 20%, such as from 1% to 15%, including from 1% to 10%, or from 1% to 5%. In some instances, the polymeric medium has a total acrylamide content of 3%.

In certain embodiments, the polymeric medium is configured to be formed from precursor moieties. For example, the polymeric medium may be a gel (e.g., a polyacrylamide gel) formed form gel precursors (e.g., polyacrylamide gel precursors, such as polyacrylamide gel monomers). The precursor moieties may be configured to react to form the polymeric medium. For instance, the gel precursors may be configured to react with each other to form the polyacrylamide gel polymeric medium. The reaction between the gel precursors may be activated by any suitable protocol, such as, but not limited to, chemical activation, light activation, etc. In some embodiments, the gel precursors are configured to be activated chemically, for example by contacting the gel precursors with an activation agent, such as, but not limited to, a peroxide. In some embodiments, the gel precursors are configured to be activated by light (i.e., photo-activated), for instance by contacting the gel precursors with light. The light may be of any wavelength suitable for activating the formation of the polymeric medium, and in some instances may have a wavelength associated with blue light in the visible spectrum. For example, the light used to activate formation of the polymeric medium may have a wavelength ranging from 400 nm to 500 nm, such as from 410 nm to 490 nm, including from 420 nm to 480 nm, or from 430 nm to 480 nm, or from 440 nm to 480 nm, or from 450 nm to 480 nm, or from 460 nm to 480 nm, or from 465 nm to 475 nm. In certain cases, the light used to activate formation of the polymeric medium has a wavelength ranging from 465 to 475 nm. In some instances, the light used to activate formation of the polymeric medium has a wavelength of 470 nm.

In certain embodiments, the polymeric medium includes a buffer. The buffer may be any convenient buffer used for gel electrophoresis. In certain embodiments, the buffer is a Tris buffer. In certain embodiments, the polymeric medium includes a buffer, such as a Tris-glycine buffer (TG buffer). For example, the buffer may include a mixture of Tris and glycine.

At least a portion of the polymeric medium (e.g., the analyte detection domain) may include a capture member stably associated therewith. By "stably associated" is meant that a moiety is non-covalently bound to or otherwise associated with another moiety or structure under standard conditions. In certain instances, the support is a polymeric medium (e.g., a polymeric gel), as described above. In certain embodiments, the capture member is non-covalently bound to the polymeric medium. Non-covalent interactions may include, but are not limited to, ionic bonds, hydrophobic interactions, hydrogen bonds, van der Waals forces (e.g., London dispersion forces), dipole-dipole interactions, and the like. In certain embodiments, the capture member is non-covalently bound to the support (e.g., polymeric medium) via a specific binding member pair. Suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like.

In certain embodiments, the capture member may be non-covalently bound to the polymeric medium through a specific binding member pair, where the polymeric medium includes one member of the specific binding member pair and the capture member includes the complementary member of the specific binding member pair. For example, the polymeric medium may include streptavidin. In some instances, the streptavidin may be copolymerized with the polymeric gel of the polymeric medium. In addition, the capture member may include the complementary member of the specific binding member pair, such as biotin. In these embodiments, contacting the biotinylated capture member to the streptavidin-polymeric medium may non-covalently bind the capture member to the polymeric medium through the specific binding interaction between the biotin of the capture member and the streptavidin of the polymeric medium. Non-covalent binding of the capture member to the polymeric medium may also be initiated via photo-activation of the capture member or the specific binding pair, such as photo-activated streptavidin or photo-activated biotin. Other complementary binding member pairs may be used as described above to non-covalently bind the capture member to the polymeric medium.

In certain embodiments, a first capture member may be non-covalently bound to the polymeric medium in a first analyte detection domain through a specific binding member pair. The polymeric medium may include one member of the specific binding member pair and the first capture member may include the complementary member of the specific binding member pair. For example, the polymeric medium may include streptavidin, which may be copolymerized with the polymeric gel of the polymeric medium as described above. In addition, the first capture member may include the complementary member of the specific binding member pair, such as biotin. In these embodiments, contacting the biotinylated first capture member to the streptavidin-polymeric medium may non-covalently bind the first capture member to the polymeric medium through the specific binding interaction between the biotin of the first capture member and the streptavidin of the polymeric medium. In some instance, the polymeric medium is configured such that the first capture member is only associated with the polymeric medium in the first analyte detection domain and not substantially associated with the polymeric medium outside of the first analyte detection domain. Other complementary binding member pairs may be used as described above to non-covalently bind the first capture member to the polymeric medium.

In certain embodiments, a second capture member may be non-covalently bound to the polymeric medium in a second analyte detection domain through a specific binding member pair. The polymeric medium may include one member of the specific binding member pair and the second capture member may include the complementary member of the specific binding member pair. For example, the polymeric medium may include streptavidin, which may be copolymerized with the polymeric gel of the polymeric medium as described above. In addition, the second capture member may include the complementary member of the specific binding member pair, such as biotin. In these embodiments, contacting the biotinylated second capture member to the streptavidin-polymeric medium may non-covalently bind the second capture member to the polymeric medium through the specific binding interaction between the biotin of the second capture member and the streptavidin of the polymeric medium. In some instance, the polymeric medium is configured such that the second capture member is only associated with the polymeric medium in the second analyte detection domain and not substantially associated with the polymeric medium outside of the second analyte detection domain. Other complementary binding member pairs may be used as described above to non-covalently bind the second capture member to the polymeric medium. Additional analyte detection domains may be provided as described above as desired. For instance, the polymeric medium may include one or more analyte detection domains, such as 2 or more, 3 or more, 4 or more, 5 or more, 6 or more, 7 or more, 8 or more, 9 or more, or 10 or more analyte detection domains.

A capture member can be any molecule that specifically binds to another binding member of interest, e.g., a protein or nucleic acid sequence or biomacromolecule that is being targeted (e.g., the analyte of interest). In some embodiments, the affinity between a capture member and its target analyte to which it specifically binds when they are specifically bound to each other in a binding complex is characterized by a $K_d$ (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. "Affinity" refers to the strength of binding, increased binding affinity being correlated with a lower $K_d$.

Depending on the nature of the analyte or interest, capture members can be, but are not limited to, (a) antigens for the detection of specific anti-antigen antibodies; (b) antibodies against an epitope of the peptidic analyte for the detection of proteins and peptides; (c) any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like.

In certain embodiments, the capture member includes a ligand of the analyte, such as an antigen. The capture member antigen may be specifically bound by an antibody of interest in an assay sample. In some cases, the capture member is stably associated (e.g., non-covalently bound) to a support (e.g., polymeric medium), as described above. The support-bound capture member may be configured to have a specific binding interaction with the analyte of interest. As such, specific binding of the analyte of interest to the support-bound capture member may indirectly bind the analyte of interest to the support. Binding of the analyte of interest to the support may stably associate the analyte with the support and thus facilitate detection of the analyte of interest.

In certain embodiments, two or more different capture members are stably associated with the polymeric medium to provide distinct detection regions that include the capture members. In certain instances, the distinct detection regions include the same capture members. In other embodiments, the distinct detection regions include different capture members. The two or more different capture members may specifically bind to the same or different analytes. In some cases, the two or more different capture members may specifically bind to different analytes. For example, the two or more capture members may include different antigens that specifically bind to different antibodies in the sample. In other cases, the two or more different capture members may specifically bind to the same analyte. For instance, the two or more different capture members may be used to detect cross-reactivity of an antibody to different antigens.

In some embodiments, the microfluidic device includes a spacer domain between adjacent analyte detection domains (e.g., the first and second analyte detection domains). In some instances, the spacer domain is configured to provide a region between analyte detection domains such that one analyte detection domain may be sufficiently distinguished from an adjacent analyte detection domain. For example, the spacer domain may include a region of the polymeric medium that does not substantially include a capture member. For instance, the spacer domain may be substantially free of a capture member. In certain cases, the polymeric medium may include a member of a specific binding member pair, such as streptavidin, as described above. In some instances, the member of the specific binding member pair is associated with its complementary binding member, where the complementary binding member is not associated with a capture member. In these instances, the member of the specific binding member pair associated with the polymeric medium may be blocked from associating with complementary binding members that are associated with a capture member.

In certain embodiments, the microfluidic device includes alternating analyte detection and spacer domains. For example, as described above, the microfluidic device may include a first analyte detection domain and a second analyte detection domain separated by a spacer domain. Additional analyte detection domains and/or spacer domains may be included in the microfluidic device as desired. As such, the microfluidic device may include analyte detection domains interspersed between spacer domains as described above. Embodiments of the microfluidic device that include alternating analyte detection domains and spacer domains may in some instances be referred to as a "barcode" assay device or an assay device with a "barcode" pattern. By "barcode" is meant a pattern as described above in which analyte detection domains, where a detectable signal may be produced, are interspersed between spacer domains, which do not include a capture moiety and thus do not produce a detectable signal.

In certain embodiments, the microfluidic device is configured to direct the sample through the polymeric medium. In some instances, the microfluidic device is configured to subject a sample to a flow field. By "flow field" is meant a region where moieties traverse the region in substantially the same direction. For example, a flow field may include a region where mobile moieties move through a medium in substantially the same direction. A flow field may include a medium, such as a polymeric medium, as described above, where moieties, such as buffers, analytes, reagents, etc., move through the medium in substantially the same direction. A flow field may be induced by an applied electric field, a pressure differential, a thermal gradient, electroosmosis, and the like. In some embodiments, the flow field may be aligned with the directional axis of the flow path of the polymeric medium. The flow field may be configured to direct the sample and/or analytes through the polymeric medium along the flow path of the polymeric medium (e.g., along the flow path of the elongated flow path of the microfluidic device).

The electric fields may facilitate the movement of the sample through the microfluidic device (e.g., electrokinetic transfer of the sample from one region of the microfluidic device to another region of the microfluidic device). For instance, the electric field may be configured to direct the analytes in a sample through the polymeric medium of the microfluidic device. The electric field may be configured to facilitate the movement of the analytes in a sample based on the physical properties of the analytes. For example, the electric field may be configured to facilitate the movement of the analytes in the sample based on the charge (e.g., charge to mass ratio or mobility), isoelectric point, etc. of the analytes. In certain instances, the electric field is configured to facilitate the movement of the analytes in the sample based on the charge of the analytes. In some cases, the electric field is configured to facilitate the movement of the analytes in the sample based on the isoelectric point of the analytes.

In some embodiments, the electric field may be directional. For example, an electric field may be aligned with the directional axis of the flow path of the polymeric medium. The electric field may be configured to direct the sample and/or analytes through the polymeric medium along the flow path of the polymeric medium.

In certain embodiments, the microfluidic device includes one or more electric field generators configured to generate an electric field. The electric field generator may be configured to apply an electric field to various regions of the microfluidic device, such as polymeric medium. The electric field generators may be configured to electrokinetically transport the analytes and moieties in a sample through the polymeric medium in the microfluidic device. In certain instances, the electric field generators may be proximal to the microfluidic device, such as arranged on the microfluidic device. In some cases, the electric field generators are positioned a distance from the microfluidic device. For example, the electric field generators may be incorporated into a system for detecting an analyte, as described in more detail below.

The microfluidic devices may include one or more channels. Embodiments of the microfluidic channels may be made of any suitable material that is compatible with the microfluidic devices and compatible with the samples, buffers, reagents, etc. used in the microfluidic devices. In some cases, the microfluidic channels are made of a substrate material that is inert (e.g., does not degrade or react) with respect to the samples, buffers, reagents, etc. used in the subject microfluidic devices and methods. For instance, the substrate may include materials, such as, but not limited to, glass (soda like glass, silica glass, etc.), quartz, silicon, polymers, elastomers, paper, combinations thereof, and the like. Other substrate material are possible, such as, but not limited to, polystyrene, polycarbonate, PDMS, cured photoresist (such as SU8) and other transparent plastics or moldable/curable polymers, thermal plastics such as Cyclo Olefin Polymer (COP, Zeonor, Zeonex, etc.), and the like.

In certain embodiments, the microfluidic channels have a width ranging from 1 µm to 500 µm, such as from 5 µm to 300 µm, including from 10 µm to 200 µm, for example from 50 µm to 150 µm. In some instances, the microfluidic channels have a width of 120 µm. In certain embodiments, the microfluidic channels have a depth ranging from 1 µm to 200 µm, such as from 5 µm to 100 µm, including from 10 µm to 50 µm. In some cases, the microfluidic channels have a depth of 35 µm. In certain embodiments, the microfluidic channels have a length ranging from 10 µm to 5 mm, such as from 50 µm to 4 mm, including from 100 µm to 3 mm, for example from 500 µm to 3 mm, or from 1 mm to 3 mm. In some cases, the microfluidic channels have a length of 2.5 mm.

In some instances, the microfluidic devices include one or more sample input ports. The sample input port may be configured to allow a sample to be introduced into the microfluidic device. The sample input port may be in fluid communication with the polymeric medium. In some instances, the sample input port is in fluid communication with the upstream end of the polymeric medium. The sample input port may further include a structure configured to prevent fluid from exiting the sample input port. For example, the sample input port may include a cap, valve, seal, etc. that may be, for instance, punctured or opened to allow the introduction of a sample into the microfluidic device, and then re-sealed or closed to substantially prevent fluid, including the sample and/or buffer, from exiting the sample input port.

In certain embodiments the microfluidic device may include two or more fluid channels in fluid communication with each other. The fluid channels may be in fluid communication with the elongated flow path described herein. In some instances, the fluid channels are configured for performing various sample preparation steps on the device (e.g., on the biochip). In other words, the microfluidic device, in some instances, may include a more complex geometry connecting two or more sample input ports (e.g., loading wells) to an elongated flow path as described herein.

In certain embodiments, the polymeric gel has a width ranging from 1 µm to 500 µm, such as from 5 µm to 300 µm, including from 10 µm to 200 µm, for example from 50 µm to 150 µm. In some cases, the polymeric gel has a width of 120 µm. In some instances, the polymeric gel has a length ranging from 10 µm to 5 mm, such as from 50 µm to 4 mm, including from 100 µm to 3 mm, for example from 500 µm to 3 mm, or from 1 mm to 3 mm. In certain instances, the polymeric gel has a length of 2.5 mm. In certain embodiments, the polymeric gel has a depth ranging from 1 µm to 200 µm, such as from 5 µm to 100 µm, including from 10 µm to 50 µm. In some cases, the polymeric gel has a depth of 35 µm.

In certain embodiments, an analyte detection domain of the polymeric gel has a length ranging from 10 µm to 1000 µm, such as from 25 µm to 900 µm, including from 50 µm to 800 µm, or from 100 µm to 700 µm, or from 200 µm to 600 µm, or from 300 µm to 600 µm, or from 400 µm to 600 µm. In some cases, the analyte detection domain of the polymeric gel has a length of 500 µm. In some cases, a spacer domain of the polymeric gel has a length ranging from 10 µm to 500 µm, such as from 50 µm to 250 µm, including from 100 µm to 250 µm. In certain embodiments, the spacer domain of the polymeric gel has a length of 200 µm.

In certain embodiments, the microfluidic device has a width ranging from 10 cm to 1 mm, such as from 5 cm to 5 mm, including from 1 cm to 5 mm. In some instances, the microfluidic has a length ranging from 100 cm to 1 mm, such as from 50 cm to 1 mm, including from 10 cm to 5 mm, or from 1 cm to 5 mm. In certain aspects, the microfluidic device has an area of 1000 $cm^2$ or less, such as 100 $cm^2$ or less, including 50 $cm^2$ or less, for example, 10 $cm^2$ or less, or 5 $cm^2$ or less, or 3 $cm^2$ or less, or 1 $cm^2$ or less, or 0.5 $cm^2$ or less, or 0.25 $cm^2$ or less, or 0.1 $cm^2$ or less.

In certain embodiments, the microfluidic device is substantially transparent. By "transparent" is meant that a substance allows visible light to pass through the substance. In some embodiments, a transparent microfluidic device facilitates detection of analytes bound to the binding medium, for example analytes that include a detectable label, such as a fluorescent label. In some cases, the microfluidic device is substantially opaque. By "opaque" is meant that a substance does not allow visible light to pass through the substance. In certain instances, an opaque microfluidic device may facilitate the analysis of analytes that are sensitive to light, such as analytes that react or degrade in the presence of light.

In some aspects, the polymeric medium is provided in an elongated flow path as described above. In these embodiments, the microfluidic device includes a channel, such as a microfluidic channel. The channel may include the polymeric medium as described above. In certain embodiments, the elongated flow path includes an interior volume defined by the sides of the elongated flow path. For example, the elongated flow path may be a channel (e.g., a microfluidic channel), which may define an interior volume of the channel. In certain instances, the polymeric medium is provided in the interior volume of the elongated flow path. For instance, the polymeric medium may be provided in substantially the entire interior volume of the functional region of the elongated flow path. The functional region of the elongated flow path is the region used for assay and detection of the sample constituents and may not include other regions of the elongated flow path, for example regions of the elongated flow path used for sample loading, buffer reservoirs, microfluidic fluid conduits, etc. are not part of the "functional region" of the elongated flow path. As described above, the polymeric medium may be provided in substantially the entire interior volume of the functional region of the elongated flow path, such that the polymeric medium substantially fills the width of the interior volume of the elongated flow path. In these embodiments, the polymeric medium substantially fills the interior volume of the elongated flow path, such that there are no significant voids in the interior volume that do not include the polymeric medium. For instance, in these embodiments, the polymeric medium is not a coating on the interior surface of the elongated flow path, but rather the polymeric medium substantially fills the interior volume of the elongated flow path. A polymeric medium that occupies substantially the entire volume of the elongated flow path may provide an increased surface area for immobilization of capture members on the polymeric medium as described above.

Methods

Embodiments of the methods are directed to determining whether an analyte is present in a sample. In certain embodiments of the methods, one or more analytes in the sample may be detected. The method includes introducing a fluid sample into an elongated flow path of the microfluidic device that includes a polymeric medium as described above. Introducing the fluid sample into the elongated flow path of the microfluidic device may include contacting the sample with the polymeric medium, or in embodiments of the microfluidic devices that include a loading medium, contacting the sample with the loading medium. The method further includes moving the sample constituents through the polymeric medium. In some cases, the movement of the sample constituents is produced by gel electrophoresis, isotachophoresis, isoelectric focusing, field amplified sample stacking, di-electrophoresis, or similar electrokinetic methods, and the like. In certain embodiments, moving the sample constituents through the polymeric medium includes applying a directional electric field to the elongated flow path (e.g., to the polymeric medium in the elongated flow path) in a manner sufficient to move components of the sample through the polymeric medium.

As the constituents in the sample move through the polymeric medium, a specific analyte of interest may be specifically bound by a capture member in the polymeric medium. For example, as described herein, the capture member may include an antigen, and as the constituents in the sample move through the polymeric medium, a specific antibody of interest may bind to the antigen and become immobilized (e.g., stably associated) with the polymeric medium.

In some cases, the immobilized analyte may then be detected. For instance, the method may include obtaining a signal from the analyte detection domain (i.e., the region of the polymeric medium that includes the capture member) to determine whether the analyte is present in the sample. In some instances, the method includes obtaining a signal from the first analyte detection domain to determine whether a first analyte is present in the sample. As described above, the microfluidic device may include one or more, such as two or more, analyte detection domains, and as such, the method may further include obtaining a signal from the second analyte detection domain to determine whether a second analyte is present in the sample. Additional analytes may be detected depending on the number of analyte detection domains included in the microfluidic device.

In certain embodiments, the method includes determining whether an analyte of interest is present in a sample, e.g., determining the presence or absence of one or more analytes of interest in a sample. In some instances, the microfluidic devices are configured to detect the presence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which a measurement of the concentration of the analyte is provided to the user.

In certain embodiments, the method includes detecting an analyte of interest bound to the polymeric medium. Detectable binding of an analyte of interest to the polymeric medium indicates the presence of the analyte of interest in the sample. In some instances, the analyte of interest includes a detectable label. The detectable label may include, but is not limited to, a fluorescent label, a colorimetric label, a chemiluminescent label, multicolor reagents, enzyme-linked reagents, avidin-streptavidin associated detection reagents, radiolabels, gold particles, magnetic labels, and the like. In some instances, the label is covalently bound to the analyte of interest.

In certain embodiments, detecting the analyte of interest includes contacting the analyte of interest with a label configured to specifically bind to the analyte of interest (e.g., a labeled secondary antibody that specifically binds to the analyte of interest). For example, detecting the analyte of interest may include contacting the analyte of interest with a labeled secondary antibody that specifically binds to the analyte of interest. Detection of the labeled secondary antibody thus indicates binding of the analyte of interest to the capture member in the analyte detection domain. In some instances, the method includes labeling the sample prior to introducing the sample into the microfluidic device. For instance, the method may include contacting the sample (e.g., the analyte of interest, or all of the constituent analytes in a biological sample or fluid) with a label prior to introducing the sample into the elongated flow path of the microfluidic device. In other embodiments, the method includes labeling the sample after to introducing the sample into the microfluidic device. For instance, the method may include introducing a label into the elongated flow path of the microfluidic device after the sample is introduced into the elongated flow path of the microfluidic device.

In certain embodiments, the method includes enhancing the detectable signal from a labeled analyte of interest. For instance, enhancing the detectable signal from a labeled analyte of interest may include contacting a labeled analyte of interest with a secondary label configured to specifically bind to the labeled analyte of interest. In certain instances, the secondary label is a labeled secondary antibody that specifically binds to the labeled analyte of interest. As such, enhancing the detectable signal from the labeled analyte of interest may include contacting the labeled analyte of interest with a labeled secondary antibody configured to specifically bind to the labeled analyte of interest. The use of two or more detectable labels as described above may facilitate the detection of the analyte of interest by improving the signal-to-noise ratio.

The secondary label can be any molecule that specifically binds to a protein or nucleic acid sequence or biomacromolecule that is being targeted (e.g., the analyte of interest). Depending on the nature of the analyte, the label can be, but is not limited to: antibodies against an epitope of a peptidic analyte (e.g., an antibody); or any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the secondary label includes a secondary antibody. The secondary antibody may specifically bind to the analyte of interest.

In certain embodiments, the secondary label includes a detectable label. Detectable labels include any convenient label that may be detected using the methods and systems, and may include, but are not limited to, fluorescent labels, colorimetric labels, chemiluminescent labels, multicolor reagents, enzyme-linked reagents, avidin-streptavidin associated detection reagents, radiolabels, gold particles, magnetic labels, and the like. In certain embodiments, the secondary label includes a secondary antibody associated with a detectable label. For example, the secondary label may include a labeled antibody (e.g., a fluorescently labeled antibody) that specifically binds to the analyte of interest.

In some embodiments, the analyte of interest can be identified so that the presence of the analyte of interest can then be detected. For instance, the method may include evaluating the polymeric medium for the presence of two or more analytes. Analytes may be identified by any of the methods described herein. For example, a labeling agent, such as an analyte specific binding member that includes a detectable label may be employed, as described above. In certain embodiments, the detectable label is a fluorescent label. Fluorescent labels are labeling moieties that are detectable by a fluorescence detector. For example, binding of a fluorescent label to an analyte of interest may allow the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.), and the like.

Suitable fluorescent molecules (fluorophores) include, but are not limited to, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoyl-carbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)aminofluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl)aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from Anthozoan species; combinations thereof; and the like.

In certain embodiments, the method includes introducing a fluid sample into a microfluidic device. Introducing the fluid sample into the microfluidic device may include directing the sample through a polymeric medium. In some cases, movement of the sample is produced by gel electrophoresis such that the sample traverses the polymeric medium, as described above. The sample may include distinct detectable analytes, where each analyte binds to a different capture member in the polymeric medium.

In certain embodiments, the method includes evaluating the polymeric medium for the presence of the analyte or analytes of interest (e.g., the two or more analytes of interest). For example, in some cases, the method includes detecting the analyte(s) bound to the polymeric medium. Detectable binding of an analyte of interest to the capture members in the polymeric medium indicates the presence of the analyte or analytes of interest in the sample. Moieties not of interest that traverse the polymeric media and do not bind to the capture members in the polymeric medium may be washed away or transferred to a secondary analysis device such as, but is not limited to, a UV spectrometer, and IR spectrometer, a mass spectrometer, an HPLC, an affinity assay device, and the like.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, different analytes may be specifically bound by different capture members in different analyte detection domains of the polymeric medium. In some instances, the number of analytes is greater than 2, such as 4 or more, 6 or more, 8 or more, etc., up to 20 or more, e.g., 50 or more, including 100 or more, distinct analytes. In certain embodiments, the methods include the multiplex analysis of 2 to 100 distinct analytes, such as 4 to 50 distinct analytes, including 4 to 20 distinct analytes.

In certain embodiments, multiplex analysis also includes the use of two or more different detectable labels. The two or more different detectable labels may specifically bind to the same or different analytes. In some cases, the two or more different detectable labels may specifically bind to the same analyte. For instance, the two or more different detectable labels may include different secondary antibodies specific for different epitopes on the same analyte. The use of two or more detectable labels specific for the same analyte may facilitate the detection of the analyte by improving the signal-to-noise ratio. In other cases, the two or more different detectable labels may specifically bind to different analytes. For example, the two or more detectable labels may include different secondary antibodies specific for epitopes on different analytes. The use of two or more detectable labels each specific for different analytes may facilitate the detection of two or more respective analytes in the sample in a single assay.

In certain embodiments, the method includes determining the presence of one or more analytes in the sample from a signal detected from a barcode assay device of the present disclosure. As described above, a "barcode" assay device is a microfluidic device of the present disclosure that includes analyte detection domains, where a detectable signal may be produced, interspersed between spacer domains, which do not include a capture moiety and thus do not produce a detectable signal. The method may include determining the presence of one or more analytes based on signal detected by the detector from a single analyte detection domain of the barcode assay device or from two or more of the analyte detection domains of the barcode assay device.

For example, the method may include obtaining signal from a single analyte detection domain and determining the presence of an analyte based on the signal from the single analyte detection domain. Once the presence or absence of the analyte is determined, the method may include determining the presence of another analyte at a different analyte detection domain. In these embodiments, the method may be used to sequentially determine the presence of an analyte by sequentially analyzing a signal from a series of analyte detection domains in the barcode assay device.

In other embodiments, the method may include determining the presence of one or more analytes substantially simultaneously. For example, the method may include determining the presence of an analyte in each analyte detection domain based on signal detected by the detector from a plurality of the analyte detection domains substantially simultaneously. In some instances, the barcode pattern of the assay device facilitates a method of obtaining signal from a plurality of analyte detection domains simultaneously. For instance, a spacer domain between adjacent analyte detection domains may facilitate distinguishing a signal from a first analyte detection domain from a signal from an adjacent analyte detection domain. As such, the method may include obtaining signal from an analyte detection domain with minimal signal interference from other analyte detection domains in the barcode assay device.

In certain embodiments, the method is an automated method. As such, the method may include a minimum of user interaction with the microfluidic devices and systems after introducing the sample into the microfluidic device. For example, the step of directing the sample through the polymeric medium may be performed by the microfluidic device and system, such that the user need not manually perform this step. In some cases, the automated method may facilitate a reduction in the total assay time. For example, embodiments of the method may be performed in 120 min or less, or 90 min or less, or 60 min or less, such as 45 min or less, or 30 min or less, such as 20 min or less, including 15 min or less, or 10 min or less, or 5 min or less.

Samples that may be assayed with the subject methods may include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analyte of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities.

In certain embodiments, the samples of interest are biological samples, such as, but not limited to, urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like. In certain embodiments, the sample is blood or a blood product, such as, but not limited to, serum, plasma, and the like. In certain embodiments, the sample is urine or saliva.

As described above, the samples that may be assayed in the subject methods may include one or more analytes of interest. Examples of detectable analytes include, but are not limited to proteins and peptides, with or without modifications, e.g., antibodies, diabodies, Fab fragments, DNA or RNA binding proteins, phosphorylated proteins (phosphoproteomics), peptide aptamers, epitopes, combinations thereof, and the like.

In certain embodiments, the method is configured to detect constituents of interest in a sample, where the sample size is small. For example, the method may be configured to detect constituents of interest in a sample, where the sample size is 1 mL or less, such as 750 µL or less, including 500 µL or less, or 250 µL or less, of 100 µL or less, or 75 µL or less, or 50 µL or less, or 40 µL or less, or 30 µL or less, or 20 µL or less, or 10 µL or less, or 5 µL or less, or 1 µL or less, or 750 nL or less, or 500 nL or less, or 250 nL or less, or 100 nL or less, or 75 nL or less, or 50 nL or less, or 25 nL or less, or 10 nL or less, or 5 nL or less, or 1 nL or less. In some instances, the method is configured to detect constituents of interest in a sample, where the sample size is 100 nL or less.

In certain embodiments, the method includes concentrating, diluting, or buffer exchanging the sample prior to directing the sample through the polymeric medium. Concentrating the sample may include contacting the sample with a concentration medium prior to contacting the sample with the polymeric medium. The concentration medium may include a small pore size polymeric gel, a membrane (e.g., a size exclusion membrane), combinations thereof, and the like. Concentrating the sample prior to contacting the sample with the polymeric medium may facilitate a decrease in the amount of concentrated sample used in an assay and/or may facilitate a decrease in the total assay time. Diluting the sample may include contacting the sample with additional buffer prior to contacting the sample with the polymeric medium. Buffer exchanging the sample may include contacting the sample with a buffer exchange medium prior to contacting the sample with the polymeric medium. The buffer exchange medium may include a buffer different from the sample buffer. The buffer exchange medium may include, but is not limited to, a molecular sieve, a porous resin, and the like.

In certain embodiments, the method includes a blocking step. As such, methods of the present disclosure may include a step of contacting the polymeric medium with a blocking reagent prior to detecting the analyte of interest, such as during fabrication of the analyte detection domains and spacer domains of the polymeric medium. In some cases, the blocking step minimizes non-specific binding of analytes to the polymeric medium. For example, the blocking step may include contacting the spacer domain with a member of a specific binding member pair (e.g., biotin) complementary to the member of the specific binding member pair (e.g., streptavidin) that is bound to the polymeric medium. In these instances, the member of a specific binding member pair (e.g., biotin) is not bound to a capture member, such that the polymeric medium in the spacer domain is not stably associated with a capture member. In these embodiments, the analyte of interest (e.g., antibody) only specifically binds to the analyte detection domain of the polymeric medium that includes the specific capture member (e.g., antigen) that the analyte of interest binds to.

In certain embodiments, the method includes optional washing steps, which may be performed at various times before, during and after the other steps in the method. For example, a washing step may be performed after binding the capture member to the polymeric medium, after contacting the sample with the polymeric medium, after contacting the polymeric medium-bound analyte of interest with a secondary label, etc.

Embodiments of the method may also include releasing the analyte bound to the polymeric medium. The releasing may include contacting the bound analyte with a releasing agent. The releasing agent may be configured to disrupt the binding interaction between the analyte and the polymeric medium. In some cases, the releasing agent is a reagent, buffer, or the like, that disrupts the binding interaction between the analyte and the capture member of the polymeric medium causing the capture member to release the analyte. After releasing the analyte from the polymeric medium, the method may include transferring the analyte away from the polymeric medium. For example, the method may include directing the released analyte downstream from the polymeric medium for secondary analysis with a secondary analysis device such as, but is not limited to, a UV spectrometer, and IR spectrometer, a mass spectrometer, an HPLC, an affinity assay device, a second microfluidic device as described herein, and the like.

Aspects of embodiments of the methods may also include methods of producing a microfluidic assay device. The method may include producing a polymeric medium in an elongated flow path of the microfluidic device. In some embodiments, the method includes producing a precursor polymeric medium in the elongated flow path. For instance, the elongated flow path may be filled with precursor moieties (e.g., gel precursors, such as polyacrylamide gel precursors). In some cases, the method includes activating the precursor moieties to form the polymeric medium. For example, activating the gel precursors may include chemically activating the gel precursors by contacting the gel precursors with an activation agent, such as, but not limited to, a peroxide. In certain cases, activating the gel precursors includes photo-activating the gel precursors by contacting the gel precursors with light. As described above, the light used to activate formation of the polymeric medium may have a wavelength of blue light in the visible spectrum. For instance, the light used to activate formation of the polymeric medium may have a wavelength ranging from 400 nm to 500 nm, such as from 410 nm to 490 nm, including from 420 nm to 480 nm, or from 430 nm to 480 nm, or from 440 nm to 480 nm, or from 450 nm to 480 nm, or from 460 nm to 480 nm, or from 465 nm to 475 nm. In certain cases, the light used to activate formation of the polymeric medium has a wavelength ranging from 465 to 475 nm. In some instances, the light used to activate formation of the polymeric medium has a wavelength of 470 nm.

In certain embodiments, the method of producing a microfluidic assay device includes producing a polymeric medium in a flow path as described above. The polymeric medium may include a first member of a specific binding pair. The method also includes introducing into the elongated flow path a defined amount of a first capture member that specifically binds to a first analyte. The first capture member includes a second member of the specific binding pair, such that the first capture member is non-covalently bound to the polymeric medium as described herein. In some instances, the first capture member is a first antigen bound to the second member of the specific binding pair. Stable association of the first capture member to the polymeric medium through the binding interaction between the members of the specific binding pair produces a first analyte detection domain that includes the first capture member non-covalently bound to the polymeric medium. Non-covalent binding of the capture member to the polymeric medium may also be initiated via photo-activation of the capture member or the specific binding pair, such as photo-activated streptavidin or photo-activated biotin. The defined amount of the first capture member is an amount sufficient to produce a first analyte detection domain having a specific desired length.

Embodiments of the method also include introducing into the elongated flow path a defined amount of the second member of the specific binding pair in a manner sufficient to produce a spacer domain. As described above, the second member of the specific binding pair in the spacer domain is not associated with a capture member. The defined amount of the second member of the specific binding pair is an amount sufficient to produce a spacer domain having a specific desired length.

Embodiments of the method also include introducing into the elongated flow path a defined amount of a second capture member that specifically binds to a second analyte. The second capture member includes a second member of the specific binding pair, such that the second capture member is non-covalently bound to the polymeric medium as described herein. In some instances, the second capture member is a second antigen bound to the second member of the specific binding pair. Stable association of the second capture member to the polymeric medium through the binding interaction between the members of the specific binding pair produces a second analyte detection domain that includes the second capture member non-covalently bound to the polymeric medium. The defined amount of the second capture member is an amount sufficient to produce a second analyte detection domain having a specific desired length.

Systems

Aspects of the present disclosure further include systems for assaying a fluid sample for the presence of two or more analytes. The systems include a microfluidic device, e.g., as described above, and a detector. In other embodiments, the system does not include a detector, for instance where detection is performed by visual detection by the user observing images of the microfluidic device or directly viewing the microfluidic device.

In some cases, the detector is a detector configured to detect a detectable label. The detector may include any type of detector configured to detect the detectable label used in the assay. As described above, detectable label may be a fluorescent label, colorimetric label, chemiluminescent label, multicolor reagent, enzyme-linked reagent, avidin-streptavidin associated detection reagent, radiolabel, gold particle, magnetic label, etc. In some instances, the detectable label is a fluorescent label. In these instances, the detector may be configured to contact the fluorescent label with electromagnetic radiation (e.g., visible, UV, x-ray, etc.), which excites the fluorescent label and causes the fluorescent label to emit detectable electromagnetic radiation (e.g., visible light, etc.). The emitted electromagnetic radiation may be detected by the detector to determine the presence of the labeled analyte bound to the polymeric medium.

In some instances, the detector may be configured to detect emissions from a fluorescent label, as described above. In certain cases, the detector includes a photomultiplier tube (PMT), a charge-coupled device (CCD), an intensified charge-coupled device (ICCD), a complementary metal-oxide-semiconductor (CMOS) sensor, a visual colorimetric readout, a photodiode, and the like.

The system may also include a source of electromagnetic radiation (i.e., an electromagnetic radiation source). In some cases, the electromagnetic radiation source is a light source. For example, the light source may include a visible light source, a UV light source, an infrared light source, etc. In some instances, the electromagnetic radiation source includes a light source, such as a UV light source. As described above, the electromagnetic radiation source may be used to apply electromagnetic radiation to the polymeric medium in the microfluidic device to covalently bond a capture member to the polymeric medium during fabrication of the polymeric medium.

In some instances, the system may be configured for a non-optical method of detection, including, but not limited to, measuring the increase of resistance of the analyte detection domains (or decrease of load current across an analyte detection domain) to determine capture of analytes of interest at the specific analyte detection domains.

Systems of the present disclosure may include various other components as desired. For example, the systems may include fluid handling components, such as microfluidic fluid handling components. The fluid handling components may be configured to direct one or more fluids through the microfluidic device. In some instances, the fluid handling components are configured to direct fluids, such as, but not limited to, fluid samples, buffers (e.g., electrophoresis buffers, wash buffers, release buffers, etc.), and the like. In certain embodiments, the microfluidic fluid handling components are configured to deliver a fluid to the polymeric medium of the microfluidic device, such that the fluid contacts the polymeric medium. The fluid handling components may include microfluidic pumps. In some cases, the microfluidic pumps are configured for pressure-driven microfluidic handling and routing of fluids through the microfluidic devices and systems disclosed herein. In certain instances, the microfluidic fluid handling components are configured to deliver small volumes of fluid, such as 1 mL or less, such as 500 μL or less, including 100 μL or less, for example 50 μL or less, or 25 μL or less, or 10 μL or less, or 5 μL or less, or 1 μL or less.

In certain embodiments, the systems include one or more electric field generators. An electric field generator may be configured to apply an electric field to various regions of the microfluidic device. The system may be configured to apply an electric field such that the sample is electrokinetically transported through the microfluidic device. For example, the electric field generator may be configured to apply an electric field to the polymeric medium. In some cases, the applied electric field may be aligned with the directional axis of the polymeric medium. As such, the applied electric field may be configured to electrokinetically transport the analytes and components in a sample through the polymeric medium. In some instances, the electric field generators are configured to apply an electric field with a strength ranging from 10 V/cm to 1000 V/cm, such as from 100 V/cm to 800 V/cm, including from 200 V/cm to 800 V/cm, or from 400 v/cm to 800 V/cm.

In certain embodiments, the system includes a power source. The power source may be a battery, such as, but not limited to a disposable or re-chargeable battery.

In certain embodiments, the subject system is a biochip (e.g., a biosensor chip). By "biochip" or "biosensor chip" is meant a microfluidic system that includes a substrate surface which displays two or more distinct microfluidic devices on the substrate surface. In certain embodiments, the microfluidic system includes a substrate surface with an array of microfluidic devices.

An "array" includes any two-dimensional or substantially two-dimensional (as well as a three-dimensional) arrangement of addressable regions, e.g., spatially addressable regions. An array is "addressable" when it has multiple devices positioned at particular predetermined locations (e.g., "addresses") on the array. Array features (e.g., devices) may be separated by intervening spaces. Any given substrate may carry one, two, four or more arrays disposed on a front surface of the substrate. Depending upon the use, any or all of the arrays may be the same or different from one another and each may contain multiple distinct microfluidic devices. An array may contain one or more, including two or more, four or more, eight or more, 10 or more, 25 or more, 50 or more, or 100 or more microfluidic devices. In certain embodiments, the microfluidic devices can be arranged into an array with an area of 100 cm$^2$ or less, 50 cm$^2$ or less, or 25 cm$^2$ or less, 10 cm$^2$ or less, 5 cm$^2$ or less, such as 1 cm$^2$ or less, including 50 mm$^2$ or less, 20 mm$^2$ or less, such as 10 mm$^2$ or less, or even smaller. For example, microfluidic devices may have dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 2 mm×2 mm or less.

Arrays of microfluidic devices may be arranged for the multiplex analysis of samples. For example, multiple microfluidic devices may be arranged in series, such that a sample may be analyzed for the presence of several different analytes in a series of microfluidic devices. In certain embodiments, multiple microfluidic devices may be arranged in parallel, such that two or more samples may be analyzed at substantially the same time. For example, multiple microfluidic devices, each including an elongated flow path as described herein, may be arranged in parallel, such that two or more samples may be analyzed at substantially the same time.

Aspects of the systems include that the microfluidic devices may be configured to consume a minimum amount of sample while still producing detectable results. For example, the system may be configured to use a sample volume of 100 µL or less, such as 75 µL or less, including 50 µL or less, or 25 µL or less, or 10 µL or less, for example, 5 µL or less, 2 µL or less, or 1 µL or less while still producing detectable results. In certain embodiments, the system is configured to have a detection sensitivity of 1 nM or less, such as 500 pM or less, including 100 pM or less, for instance, 1 pM or less, or 500 fM or less, or 250 fM or less, such as 100 fM or less, including 50 fM or less, or 25 fM or less, or 10 fM or less. In some instances, the system is configured to be able to detect analytes at a concentration of 1 µg/mL or less, such as 500 ng/mL or less, including 100 ng/mL or less, for example, 10 ng/mL or less, or 5 ng/mL or less, such as 1 ng/mL or less, or 0.1 ng/mL or less, or 0.01 ng/mL or less, including 1 pg/mL or less. In certain embodiments, the system has a dynamic range from $10^{-18}$ M to 10 M, such as from $10^{-15}$ M to $10^{-3}$ M, including from $10^{-12}$ M to $10^{-6}$ M.

In some cases, the system is configured to have a signal-to-noise ratio (SNR) of 10 or more, such as 15 or more, including 20 or more, or 30 or more, or 40 or more, or 50 or more, or 60 or more, or 70 or more, or 80 or more, or 90 or more, or 100 or more, or 150 or more, or 200 or more, or 500 or more, or 1,000 or more, or 2,000 or more, or 3,000 or more, or 4,000 or more, or 5,000 or more, or 6,000 or more, or 7,000 or more, or 8,000 or more, or 9,000 or more, or 10,000 or more. In some cases, the achievable signal-to-noise ratio depends on the method of detection used in the assay. For example, in certain embodiments the analyte of interest is directly labeled with a detectable label. In these embodiments, the signal-to-noise ratio may be 10 or more, such as 15 or more, including 20 or more, or 30 or more, or 40 or more, or 50 or more, or 60 or more, or 70 or more, or 80 or more, or 90 or more, or 100 or more, or 150 or more, or 200 or more. In other embodiments, the analyte of interest is first labeled with a primary label (e.g., a primary antibody) and then the primary label is labeled with a secondary label (e.g., a secondary antibody). In these embodiments, the signal-to-noise ratio may be 100 or more, such as 150 or more, including 200 or more, or 500 or more, or 1,000 or more, or 2,000 or more, or 3,000 or more, or 4,000 or more, or 5,000 or more, or 6,000 or more, or 7,000 or more, or 8,000 or more, or 9,000 or more, or 10,000 or more.

In certain embodiments, the microfluidic devices are operated at a temperature ranging from 1° C. to 100° C., such as from 5° C. to 75° C., including from 10° C. to 50° C., or from 20° C. to 40° C. In some instances, the microfluidic devices are operated at a temperature ranging from 35° C. to 40° C.

In certain embodiments, systems of the present disclosure include a microfluidic device configured to assay a sample to produce a detectable signal and a signal processing module configured to determine the presence of an analyte in the sample from the detected signal. As described above, systems of the present disclosure may also include a detector. In some instances, the signal processing module is configured to receive a signal from the detector and output a result of whether an analyte is present in the sample. The signal processing module may be integrated into the microfluidic device and/or detector as a single device, or may be separate from the microfluidic device and/or detector where the signal processing module and the detector are in communication with each other, e.g., via a wired or wireless communication protocol.

In certain embodiments, the signal processing module is configured to determine the presence of one or more analytes in the sample from a signal detected from a barcode assay device of the present disclosure. As described above, a "barcode" assay device is a microfluidic device of the present disclosure that includes analyte detection domains, where a detectable signal may be produced, interspersed between spacer domains, which do not include a capture moiety and thus do not produce a detectable signal. The signal processing module may be configured to determine the presence of one or more analytes based on signal detected by the detector from a single analyte detection domain of the barcode assay device or from two or more of the analyte detection domains of the barcode assay device.

For example, the signal processing module may be configured to determine the presence of an analyte based on signal detected by the detector from a single analyte detection domain. Once the presence or absence of the analyte is determined, the signal processing module may determine the presence of another analyte at a different analyte detection domain. In these embodiments, the signal processing module may be configured to sequentially determine the presence of an analyte by sequentially analyzing a signal from a series of analyte detection domains in the barcode assay device.

In other embodiments, the signal processing module may be configured to determine the presence of one or more analytes substantially simultaneously. For example, the signal processing module may be configured to determine the presence of an analyte in each analyte detection domain based on signal detected by the detector from a plurality of the analyte detection domains substantially simultaneously. In some instances, the barcode pattern of the assay device facilitates detecting signal from a plurality of analyte detection domains simultaneously. For instance, a spacer domain between adjacent analyte detection domains may facilitate distinguishing a signal from a first analyte detection domain from a signal from an adjacent analyte detection domain. As such, the signal processing module may be configured to determine the presence of an analyte in an analyte detection domain with minimal signal interference from other analyte detection domains in the barcode assay device.

Aspects of the present disclosure further include systems, e.g., computer based systems, which are configured to detect the presence of an analyte in a sample, e.g., as described above. A "computer-based system" refers to the hardware, software, and data storage device used to analyze the signal data from the microfluidic device. In some instances, the hardware of the computer-based systems of the present disclosure includes a central processing unit (CPU), an input device, an output device, and a data storage device. For example, an input device may include a device configured to allow a user to input information and/or commands into the system to interact with or control the system, such as but not limited to, a keyboard, a graphical interface input device (e.g., a mouse, touch-sensitive input device, etc), and the like. An output device may include a device configured to display or otherwise communicate information to a user, such as the results of the assay, and may include, but is not limited to, devices such as a display, an audio output device, and the like. The data storage device may include a computer readable storage medium that includes a recording of the data as described above, or a memory access device that can access such a computer readable storage medium.

To "record" data, programming or other information on a computer readable storage medium refers to a process for storing information on the computer readable storage medium such that the information may be retrieved at a subsequent point in time. Any convenient data storage structure may be used, based on the access device used to access the stored information. A variety of data processor programs and formats can be used for storage, e.g., word processing text file, spreadsheet format, database format, combinations thereof, and the like.

A "processor" refers to hardware and/or software configured to execute programmed functions for operating the devices and systems and performing the methods as disclosed herein. For example, a processor may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, an optical disk or solid state memory device may include the programming recorded thereon, and can be read by a suitable access device which is configured to communicate with the processor.

In certain embodiments, the subject systems include the following components: (a) a communication module configured to transfer information between the system and one or more users, e.g., via a user computer, as described below; and (b) a processor configured to perform one or more tasks involved in the qualitative and/or quantitative analysis methods of the present disclosure. In some instances, the communication module may be configured to transfer information to one or more remote users using a wireless transmission device. For example, the system may be configured to be portable, such that the microfluidic device may be used in the field or at a particular remote location and transmit data to one or more users at another site, such that the data may be analyzed at a location remote from where the microfluidic device is being used.

In certain embodiments, the system includes a computer readable medium having control logic (e.g., a computer software program, including program code) stored thereon. The control logic, when executed by the processor of the computer, causes the processor to perform functions described herein. In other embodiments, some functions are implemented primarily in hardware using, for example, a hardware state machine. Implementation of the hardware state machine so as to perform the functions described herein may be accomplished using any convenient methods.

In addition to the detector and the signal processing module, e.g., as described above, systems of the present disclosure may include additional components, such as, but not limited to, data output devices, e.g., monitors and/or speakers, data input devices, e.g., interface ports, keyboards, etc., fluid handling components, power sources, etc.

Utility

The subject devices, systems and methods find use in a variety of different applications where determination of the presence or absence, and/or quantification of one or more analytes in a sample is desired. In certain embodiments, the methods are directed to the detection of nucleic acids, proteins, or other biomolecules in a sample. For example, embodiments of the devices, systems and methods of the present disclosure find use in assay platforms that can be used to identify pathogens, immune reactions or presence of biochemical agents, environmental and water pathogen monitoring and detection, food safety, and bio-agricultural analysis. The ability to define distinct analyte detection domains inside microfluidic devices serves as the basis for a variety of analytical platforms. For instance, microfluidic devices that include distinct, heterogeneous analyte detection domains as described herein find use in multiplexed assays and experiments. Localized patterning of capture members in the analyte detection domains facilitates the production of bioanalytical devices for these multiplexed assays and experiments.

The devices, systems and methods of the present disclosure find use in the detection of proteins, peptides, nucleic acids, and the like. In some cases, the subject devices, systems and methods find use in the detection of proteins, such as, but not limited to antibodies. In certain embodiments, the detection of antibodies in a sample can be an indication of an underlying disease or condition, where a subject produces such antibodies in response to the disease or condition. As such, the devices, systems and methods of the present disclosure find use in the detection and diagnosis of a disease condition in a subject (e.g., human or animal) by detecting antibodies associated with the disease condition.

The devices, systems and methods of the present disclosure find use in the detection of a set of biomarkers, e.g., two or more distinct protein biomarkers, in a sample. For example, the devices, systems and methods may be used in the rapid, clinical detection of two or more disease biomarkers in a biological sample, e.g., as may be employed in the diagnosis of a disease condition in a subject, in the ongoing management or treatment of a disease condition in a subject, etc. In addition, the subject devices, systems and methods find use in protocols for the detection of an analyte in a sample, such as, but not limited to, Western blotting, Southern blotting, Northern blotting, Eastern, Far-Western blotting, Southwestern blotting, and the like.

In some cases, the subject devices, systems and methods may be used to detect the presence or absence of particular analytes (also referred to herein as biomarkers), as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject devices, systems and methods. Furthermore, the early detection of biomarkers associated with diseases is facilitated by the high sensitivity of the subject devices and systems, as described above. Due to the capability of detecting multiple biomarkers on a single chip, combined with sensitivity, scalability, and ease of use, the presently disclosed microfluidic devices, systems and methods finds use in portable and point-of-care or near-patient molecular diagnostics.

In certain embodiments, the subject devices, systems and methods find use in detecting biomarkers for an infectious disease or disease state. In some cases, the biomarkers can be molecular biomarkers, such as but not limited to proteins, nucleic acids, carbohydrates, small molecules, and the like. For example, the subject devices, systems and methods may be used to monitor HIV viral load and patient CD4 count for HIV/AIDS diagnosis and/or therapy by detecting antibodies to HIV capsid protein p24, glycoprotiens 120 and 41, CD4+ cells, and the like. Particular diseases or disease states that may be detected by the subject devices, systems and methods include, but are not limited to, bacterial infections, viral infections, increased or decreased gene expression, chromosomal abnormalities (e.g. deletions or insertions), and the like. For example, the subject devices, systems and methods can be used to detect gastrointestinal infections, such as but not limited to, aseptic meningitis, botulism, cholera, *E. coli* infection, hand-foot-mouth disease, *helicobacter* infection, hemorrhagic conjunctivitis, herpangina, myocaditis, paratyphoid fever, polio, shigellosis, typhoid fever, *vibrio* septicemia, viral diarrhea, etc. In addition, the subject devices, systems and methods can be used to detect respiratory infections, such as but not limited to, adenovirus infection, atypical pneumonia, avian influenza, swine influenza, bubonic plague, diphtheria, influenza, measles, meningococcal meningitis, mumps, parainfluenza, pertussis (i.e., whooping cough), pneumonia, pneumonic plague, respiratory syncytial virus infection, rubella, scarlet fever, septicemic plague, severe acute respiratory syndrome (SARS), tuberculosis, etc. In addition, the subject devices, systems and methods can be used to detect neurological diseases, such as but not limited to, Creutzfeldt-Jakob disease, bovine spongiform encephalopathy (i.e., mad cow disease), Parkinson's disease, Alzheimer's disease, rabies, etc. In addition, the subject devices, systems and methods can be used to detect urogenital diseases, such as but not limited to, AIDS, chancroid, *Chlamydia*, condyloma accuminata, genital herpes, gonorrhea, lymphogranuloma venereum, non-gonococcal urethritis, syphilis, etc. In addition, the subject devices, systems and methods can be used to detect viral hepatitis diseases, such as but not limited to, hepatitis A, hepatitis B, hepatitis C, hepatitis D, hepatitis E, etc. In addition, the subject devices, systems and methods can be used to detect hemorrhagic fever diseases, such as but not limited to, Ebola hemorrhagic fever, hemorrhagic fever with renal syndrome (HFRS), Lassa hemorrhagic fever, Marburg hemorrhagic fever, etc. In addition, the subject devices, systems and methods can be used to detect zoonosis diseases, such as but not limited to, anthrax, avian influenza, brucellosis, Creutzfeldt-Jakob disease, bovine spongiform encephalopathy (i.e., mad cow disease), enterovirulent *E. coli* infection, Japanese encephalitis, leptospirosis, Q fever, rabies, sever acute respiratory syndrome (SARS), etc. In addition, the subject devices, systems and methods can be used to detect arbovirus infections, such as but not limited to, Dengue hemorrhagic fever, Japanese encephalitis, tick-borne encephalitis, West Nile fever, Yellow fever, etc. In addition, the subject devices, systems and methods can be used to detect antibiotics-resistance infections, such as but not limited to, *Acinetobacter baumannii, Candida albicans, Enterococci* sp., *Klebsiella pneumoniae, Pseudomonas aeruginosa, Staphylococcus aureus*, etc. In addition, the subject devices, systems and methods can be used to detect vector-borne infections, such as but not limited to, cat scratch disease, endemic typhus, epidemic typhus, human ehrlichosis, Japanese spotted fever, louse-borne relapsing fever, Lyme disease, malaria, trench fever, Tsutsugamushi disease, etc. Similarly, the subject devices, systems and methods can be used to detect cardiovascular diseases, central nervous diseases, kidney failures, diabetes, autoimmune diseases, sickle-cell disease, Cytomegalovirus, biological fluid or tumor biopsy biomarkers for cancer (oncology), and many other diseases.

The subject device, systems and methods find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The subject devices, systems and methods also find use in validation assays. For example, validation assays may be used to validate or confirm that a potential disease biomarker is a reliable indicator of the presence or absence of a disease across a variety of individuals. The short assay times for the subject devices, systems and methods may facilitate an increase in the throughput for screening a plurality of samples in a minimum amount of time.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the weight and operating cost are less than the typical stationary laboratory equipment. The subject systems and devices may be integrated into a single apparatus, such that all the steps of the assay, including separation, transfer, labeling and detecting of an analyte of interest, may be performed by a single apparatus. For example, in some instances, there are no separate apparatuses for separation, transfer, labeling and detecting of an analyte of interest. In addition, the subject systems and devices can be utilized in a home setting for over-the-counter home testing by a person without medical training to detect one or more analytes in samples. The subject systems and devices may also be utilized in a clinical setting, e.g., at the bedside, for rapid diagnosis or in a setting where stationary research laboratory equipment is not provided due to cost or other reasons.

Kits

Aspects of the present disclosure additionally include kits that have a microfluidic device as described herein. Embodiments of the kits also include a packaging configured to contain the microfluidic device. The packaging may be a sealed packaging. For example, in certain embodiments, the kits include a sealed package configured to maintain the sterility of the microfluidic device. The sealed package may be sealed such that substantially no external contaminants, such as dirt, microbes (e.g., fungi, bacteria, viruses, spore forms, etc.), liquids, gases, and the like, are able to enter the sealed package. For example, the sealed package may be sealed such the package is water-tight and/or air-tight.

The kits may further include a buffer. For instance, the kit may include a buffer, such as an electrophoretic buffer, a sample buffer, and the like. The kits may further include additional reagents, such as but not limited to, release agents, denaturing agents, refolding agents, detergents, detectable labels (e.g., fluorescent labels, colorimetric labels, chemiluminescent labels, multicolor reagents, enzyme-linked reagents, avidin-streptavidin associated detection reagents, radiolabels, gold particles, magnetic labels, etc.), and the like. In some instances, the kit may include a labeling reagent that specifically binds to an analyte. For instance, as described above, a labeling reagent may be used to provide a detectable label for a specific analyte of interest that is specifically bound by a capture member in the device.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another form would be a computer readable medium, e.g., CD, DVD, Blu-Ray, computer-readable memory, etc., on which the information has been recorded or stored. Yet another form that may be present is a website address which may be used via the Internet to access the information at a removed site. Any convenient means may be present in the kits.

Aspects of the present disclosure additionally include kits that have a microfluidic device as described in detail herein. The kits may further include a buffer. For instance, the kit may include a buffer, such as an electrophoretic buffer, a sample buffer, and the like. The kits may further include additional reagents, such as but not limited to, release agents, denaturing agents, refolding agents, detergents, detectable labels (e.g., fluorescent labels, colorimetric labels, chemiluminescent labels, multicolor reagents, enzyme-linked reagents, avidin-streptavidin associated detection reagents, radiolabels, gold particles, magnetic labels, etc.), and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Example 1

I. Summary

Experiments were performed using a point-of-care microfluidic 'bar code' assay for antibodies to viral infection. By "bar code" is meant that the microfluidic device includes multiple distinct analyte detection domains as described herein. To create an antigen binding site bar code in a single microchannel (no junctions), high density 3D antigen immobilization via ordered electrophoretic patterning steps was used. Electrophoretic introduction of biotin-labeled capture antigen non-covalently bound to a streptavidin acrylamide hydrogel. Multiplexed antibody detection times were reduced from 4 hours to 10 minutes with <1 femtomole lower limit of detection in human sera.

II. Experimental

Figure 4:
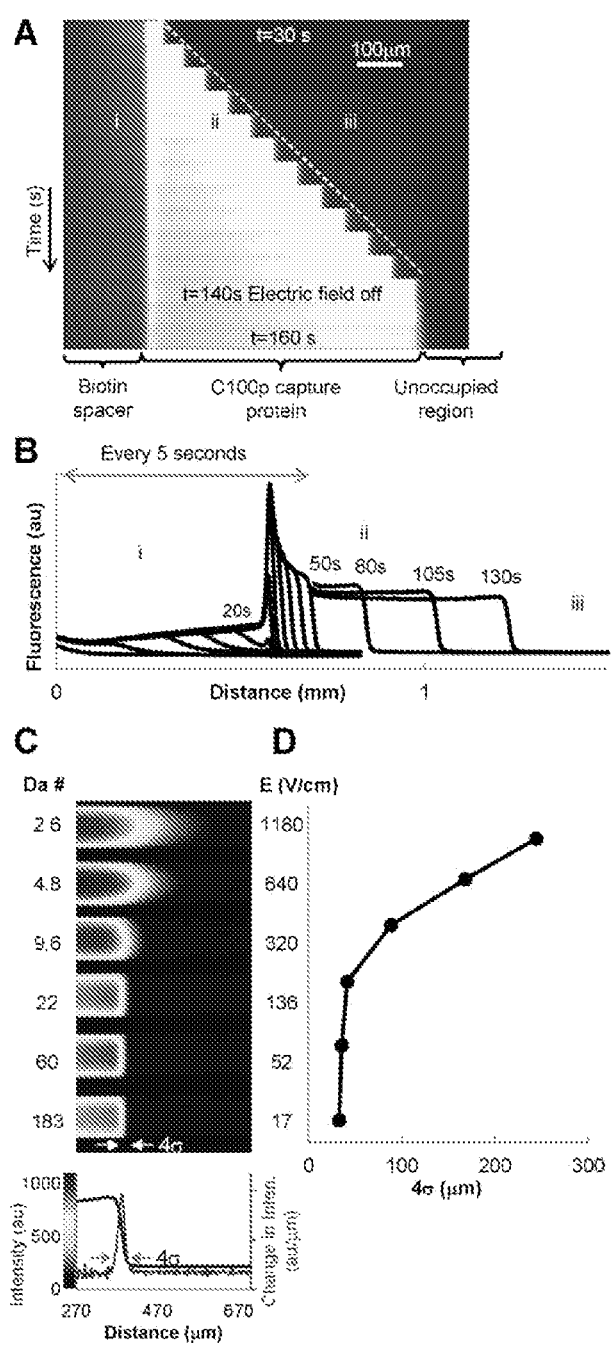
FIG. 4 shows characterization and optimization of the electrophoretic barcode patterning process, according to embodiments of the present disclosure.

A. Bar Code Patterning of Hydrogels Using Electrophoresis:

To create the bar code assays, a streptavidin-acrylamide monomer was cross-linked via photopatterning to create a polyacrylamide gel, filling a microchannel in a glass chip (FIG. 1(A)). Bar code antigen patterning was then performed using ordered electrophoretic introduction of biotinylated antigen to the streptavidin (SA) decorated gel (FIG. 1(B)). Antigens entering the channel only electromigrated further into the channel if SA sites at locations closest to the introduction well were fully saturated. The length of an immobilized antigen zone was controlled by the duration of injection and flux of electrophoretically injected material where the flux depended on the mobility, applied electric field and initial concentration. As shown in FIG. 1(A) and FIG. 1(B), 4 µM of SA in the gel provided 16 µM of biotinylated antigen capture sites leading to a 3.2× enrichment of 5 µM HCV-c100p antigen during the immobilization. The 3D hydrogel structure provided 100-1000 fold higher capture sites compared to surface patterning approaches. Cross reactivity tests showed that each antibody was captured in its corresponding antigen zone. The straight channel geometry allowed multiplexed device layouts (6 devices/cm$^2$). Custom antigen patterning and assay steps were automated through voltage application. Using the bar code approach, a multiplexed assay device that included 4 unique antigen bands in a 2.5 mm long channel with open spacer regions between the binding bands was produced (FIGS. 1(A)-1(B)). Antibodies electrophoretically injected from the right were captured in the right edge of the antigen band as expected (FIG. 1(C)).

B. Detection of Hepatitis C Antibodies:

Patterning of two HCV antigens, HCV-NS3 and HCV-c100p, allowed detection of HCV antibodies in human sera. Hepatitis C antibodies were detected at clinically relevant levels (0.025-100 µg/mL) in assay times compatible with near-patient operation (30 minutes compared to 8 hours with conventional HCV confirmatory diagnostics) (FIG. 1(D)). For c100p antibodies, the lower limit of detection (LLOD) was 25 ng/ml (sera), corresponding to 0.75 femtomole antibody detected. LLOD values were in ranges similar to those of bench top Western blot and immunoblot techniques.

Example 2

Summary

Experiments were performed using a simple 'single inlet, single outlet' microchannel architecture with multi analyte detection capability. A streptavidin-functionalized, channel-filling polyacrylamide gel in a simple glass microchannel operated as a 3D scaffold for an electrophoretic, heterogeneous immunoassay. Biotin and biotinylated capture reagents were patterned in discrete regions along the axis of the microchannel. Alternating capture reagent regions with biotin blocked regions resulted in a barcode-like pattern of analyte detection domains and spacers along the channel. To optimize barcode fabrication, an empirical study of patterning behavior was conducted across a range of electromigration and binding reaction timescales. The heterogeneous barcode immunoassay was used to detect human antibodies against HCV and HIV antigens. Serum was electrophoresed through the barcode patterned gel, allowing capture of antibody targets. Assay performance was assessed across a range of Damkohler numbers. Compared to immunoblots that require 4-10 hour sample incubation steps with concomitant 8-20 hour total assay durations, directed electromigration and reaction in the subject microfluidic barcode assay led to a 10 min sample incubation step and a 30 minute total assay duration. Further, the barcode assay reported clinically relevant sensitivity (25 ng/ml in 2% human sera) that was comparable to standard HCV confirmatory diagnostics. Given the low voltage, low power and automated operation, the subject microfluidic barcode assay finds use in rapid confirmatory diagnostics for near-patient settings.

Experiments were performed using a 'single inlet, single outlet' electrophoretic fabrication approach that allowed barcode patterning of multiple capture antigens along the length of one channel. Distinct capture reagents (antigens) and non-reactive spacer regions were patterned in the 2.5 mm long channel. The multiplexed microfluidic barcode assay was used for detection of immunoglobulin specific for HCV-c100p, HCV-NS3 and HIV-I p24 antigens—a multi-biomarker panel for diseases with high co-infection rates. The single microchannel barcode assay was completed in 30 minutes with an analytical sensitivity and specificity comparable to the 6+ hour RIBA 3.0 assay. Assay operation was solely electronic at the one inlet and one outlet, with electrophoresis conducted at low applied voltages, thus eliminating the dependence on high voltage power supplies, pumps, syringes, or valves—making the device useful for near-patient operation.

Materials and Methods

Reagents

HCV positive pooled human plasma derived HCV Core, NS3 and c100p antibodies (AF-568 conjugated and unconjugated), and recombinant HCV Core, NS3 and c100p antigens and their biotin and AF488 conjugated formats were provided by Novartis Diagnostics (Emeryville, Calif.). HIV p24 antigen and HIV p24 mouse antibodies were purchased from Prospec-Tany Technogene (Rehovot, Israel). Biotin conjugated protein-L was purchased from Thermo Fisher Scientific (Rockford, Ill.). Biotin and Biotin-FITC were purchased from AnaSpec (Fremont, Calif.). Streptavidin-acrylamide, and AF-568 conjugated anti-human and anti-mouse secondary goat antibodies were purchased from Invitrogen (Carlsbad, Calif.). HCV-HIV negative human sera were purchased from SeraCare Life Sciences (Oceanside, Calif.). All antibody, antigen and serum samples were diluted in 1× Tris-glycine (TG) buffer purchased in 10× strength from Bio-Rad (Hercules, Calif.).

VA-086 photoinitiator (2,2-azobis[2-methyl-N-(2-hydroxyethyl) propionamide]) was purchased from Wako Chemicals (Richmond, Va.). 30:1 Acrylamide-bisacrylamide monomer solution, glacial acetic acid, methanol and 3-(trimethoxysilyl)-propyl methacrylate (Silane 174) were purchased from Sigma-Aldrich (St. Louis, Mo.).

Imaging, Data Acquisition and Chip Operation

Images were captured via a Peltier-cooled CCD camera (Cool Snap HQ2, Roper Scientific, Trenton, N.J.) attached to an Olympus IX-50 epi-fluorescence microscope (Center Valley, Pa.) equipped with 10× objective (UPlanFL, N.A.=0.3, Olympus, Center Valley, Pa.), and GFP (41017 FL-CUBE ENDOW) and DSRED (XF111-2-CSM; OMEGA FL) filters (Omega Optical, Battleboro, Vt.). A 100 W mercury arc lamp was used as the excitation source. Semi-automated image capture was controlled through Metamorph software by Molecular Devices LLC (Sunnyvale, Calif.) installed on a PC (Dell Inc. Round Rock, Tex.). Exposure times with 4×4 pixel binning varied between 5 ms-400 ms depending on the experiment. Post-processing and analysis of the images were performed with ImageJ (NIH, Bethesda, Calif.) and Matlab (Mathworks, Natick, Mass.). A custom built, computer controlled, 8 channel current or voltage programmable high voltage power supply (HVPS) was used.

Chip and Gel Fabrication

Chips were designed in-house and fabricated in soda lime glass substrates by Caliper Life Sciences (Hopkinton, Mass.) utilizing standard wet silica etching methods and thermal bonding. Seven straight channels were included on each chip (FIG. 2(A)). Channels were 2.5 mm long, 35 μm deep and 120 μm wide. Two millimetre diameter, 1 mm deep reservoirs for sample and electrical connectivity were located at each channel terminus.

Before PA gel fabrication, channel walls were functionalized for enhanced gel to wall attachment. Before the functionalization step, channels were cleaned with 1M NaOH for 10 minutes, followed by 3 DI-water wash steps. To generate the silane monolayer coating on the channel walls, channels were incubated with a premixed, degassed and agitated solution of 2:3:2 silane-water-acetic acid for 30 minutes. Incubation was performed at room temperature with the chip sitting in a covered petri dish with a wet tissue to prevent evaporation of the silane solution in the wells. After the monolayer formation, silane solution was washed out of the channels with methanol for 5 minutes followed by two rounds of methanol and then water washes. After the final wash step, channels were aspirated and then purged with $N_2$ gas. Gel precursor solution was prepared in 1×TG buffer with 3% T acrylamide/bisacrylamide (30:1), 4 μM streptavidin acrylamide (SA) and 2 mg/ml VA-086 photoinitiator. Degassed and agitated solution (10 min sonication with vacuum applied to the tube) was wicked into the microchannels in 1-2 s. Polymerization of streptavidin-PA gel was performed via flood UV exposure with a UV lamp (UVP B100-AP, Upland, Calif.) enclosed in an air-cooled box for 10 minutes at 10 mW/cm$^2$ power settings. The chip was placed in a humidified petri dish. Following polymerization, chips were visually inspected for gel defects. If defects in the gel were detected, the chip was discarded. After polymerization, excess gel in the wells was removed with a pipette tip attached to vacuum. Chips were stored at 4° C. in a humidified petri dish, as described. Following the completion of experiments, chips were disinfected with 5% bleach solution. Gel was removed using a perchloric acid-hydrogen peroxide solution used with appropriate safety controls.

Antigen Immobilization and Assay Operation

Figure 2:
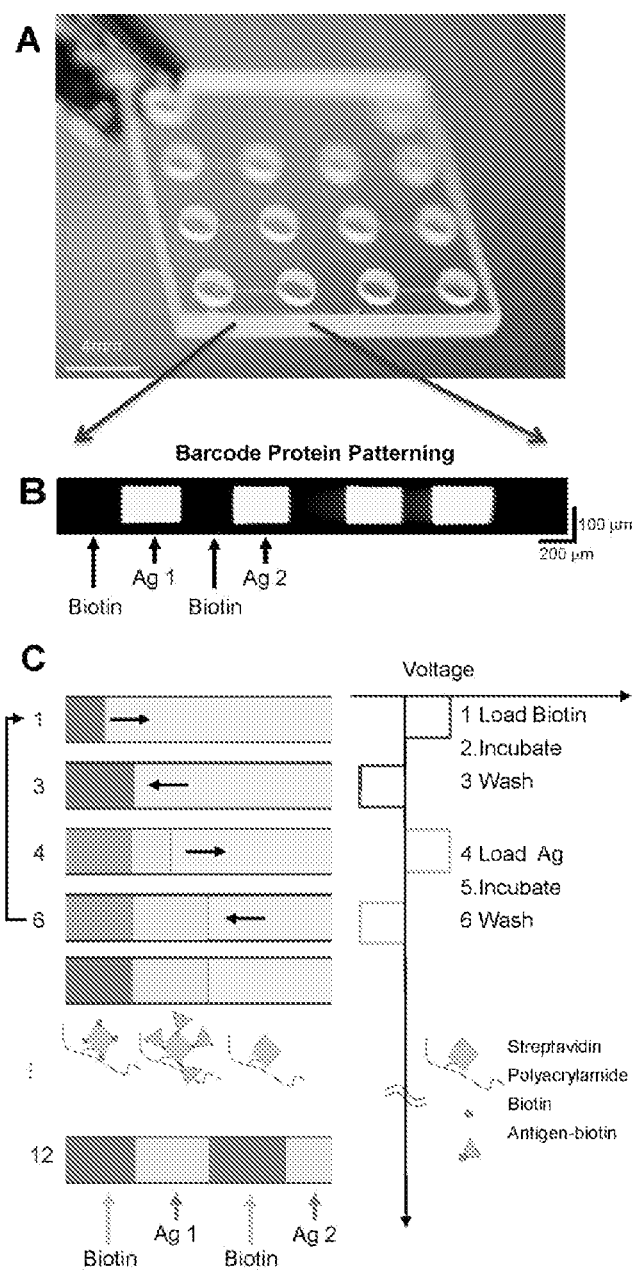
FIG. 2 shows a microfluidic barcode assay for multiplexed protein detection according to embodiments of the present disclosure.
Figure 3:
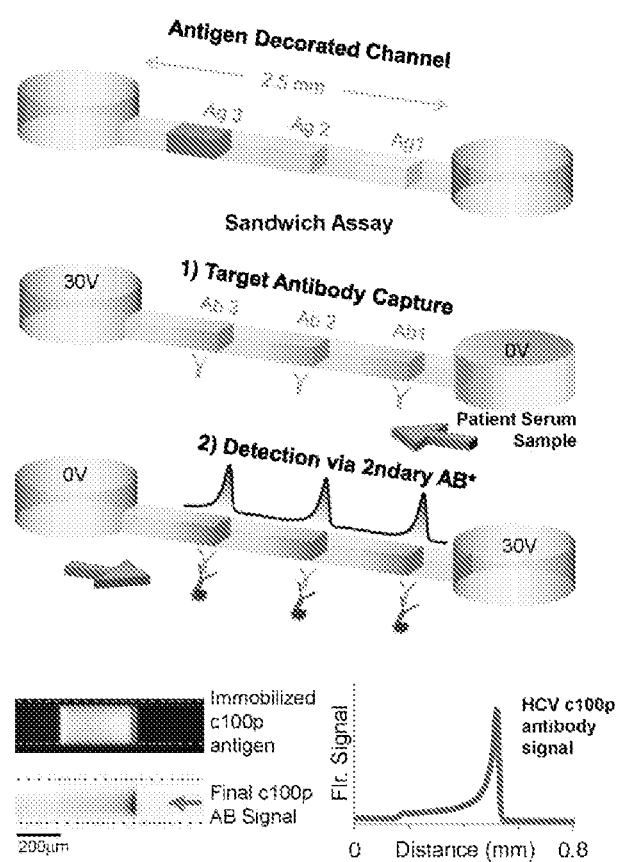
FIG. 3 shows a schematic of an antibody sandwich assay: Serum sample was electrophoretically delivered to the channel sieves through decorated antigen zones where corresponding target antibodies were captured. In a following step, detection was performed with fluorescently labelled antihuman secondary antibodies loaded electrophoretically. The bottom images show the antibody signal from a 2% human serum sample spiked with 1 µg/ml HCV-c100p antibody, according to embodiments of the present disclosure. Fluorescent detection was performed using AF-568 labelled antihuman goat antibodies.

After gel preparation, the streptavidin-PA gel-filled microchannels were electrophoretically patterned with barcode-like patterns of biotinylated antigens (FIG. 2(B)). An overview of the patterning process is detailed in FIG. 2(C) and Table 1 below. Similar to the reagent-spacer patterning, assay operation was performed electrophoretically and described in FIG. 3 and Table 2 below. Human serum sample diluted in TG buffer was electrophoretically delivered to the immobilized antigen zones. As target antibodies electromigrated through the reagent patterned gel, target antibodies were captured in the corresponding antigen zone. After flushing antibody out of the channel, fluorescently labelled secondary anti-human antibodies were introduced for optical detection of bound primary antibodies.

TABLE 1

Polymeric medium patterning process steps

| Step | Sample | Duration (min) | Voltage (V) | Current (μA) | Energy (Watt-hour) |
|---|---|---|---|---|---|
| 1 Load | 20 uM Biotin | 1 | 1.5 | 0.15 | 3.75E−09 |
| 2 Incubate | | 1 | 0 | 0 | |
| 3 Reverse Wash | TG buffer | 2 | −18 | −2 | 1.20E−06 |
| 4 Load | 5 uM c100p-biotin | 2 | 9 | 1 | |
| 5 Incubate | | 1 | 0 | 0 | |
| 6 Reverse Wash | TG buffer | 2 | −18 | −2 | 1.20E−06 |
| ... Repeat 1-6 for the next agents | | | | | |
| 49 Reverse Load | 20 uM Biotin | 2 | 18 | 2 | 1.20E−06 |
| 50 Incubate | | 1 | 0 | 0 | |
| 51 Final wash | TG buffer | 3 | 18 | 2.8 | 2.52E−06 |
| | Total duration for 4 Ag zones | 60 minutes | | Total energy (Watt hour) | 1.81E−05 |

Table 1 shows antigen patterning parameters for four sets of antigen bands interlaced with biotin spacers in a channel. Depending on the mobility and the concentration of the antigen-biotin, duration of the loading step and corresponding loading voltage were adjusted for the desired band length. Before any step involving a new solution, wells were washed with TG buffer 3 times.

TABLE 2

Assay operation steps

| Step | | Sample | Duration (min) | Voltage (V) | Current (µA) | Energy (Watt-hour) |
|---|---|---|---|---|---|---|
| 1 | Sample Load | 2% serum sample | 5 | 30 | 3.5 | 8.75E−06 |
|   | Sample Load | 2% serum sample | 5 | 30 | 3.5 | 8.75E−06 |
| 2 | Wash | TG buffer | 2.5 | −30 | −2.8 | 3.50E−06 |
| 3 | 2ndary AB (AF-568) Load | 40 µg/ml in TG | 3.5 | −40 | −5.3 | 1.24E−05 |
| 4 | Wash | TG buffer | 2.5 | 30 | 2.8 | 3.50E−06 |
|   | Wash | TG buffer | 2.5 | 30 | 2.8 | 3.50E−06 |
|   |   | Total duration | 21 minutes |   | Total energy (Watt hour) | 4.04E−05 |

Table 2 shows serological assay parameters. 21 minutes of the 30 minute assay time was automated. 5-10 minutes of manual intervention included sample loading and washing of the wells. In the first step, 3 µl sample (HCV-c100p human antibodies spiked in 2% serum in TG buffer) was refreshed at the end of 5 minute loading. Similarly the wash buffer (TG) at the final stage (step 4) was refreshed at the 2.5 minute interval.

Before each wash step run and secondary antibody load, wells were cleaned with TG buffer 3 times. Three independent assays were run together. For detection, AF-568 labeled antihuman goat antibodies were used. Total energy consumption was $4.04\times10^{-5}$ Watt-hours. 3×9V batteries hold 15 Watt-hour of energy, which would provide $3\times10^5$ possible assays.

Results and Discussion

Fabrication of Barcode Assay Format Depends on Competition Between Reaction and Electromigration Experiments were performed to determine the feasibility of a purely electrophoretic heterogeneous immunoassay in a one inlet and one outlet microchannel: a microfluidic "barcode" assay (FIG. 2(A)). In this heterogeneous immunoassay, the immobilized phase was a capture protein used to probe for an antibody in a biospecimen sample. The fabrication and assay were designed to be controlled using only an applied electric potential (e.g., no pumps, values). The patterning principle depended on two parameters present when biotinylated proteins electromigrate through a channel-filling streptavidin-PA gel. Namely, that the biotinylated capture protein will either freely electromigrate along the channel axis (e.g., in cases where the streptavidin-PA gel is already saturated with biotin, no patterning of capture protein) or the biotinylated capture protein will bind to streptavidin resulting in protein immobilization (patterning) (FIG. 2(B)). The multiplexed barcode patterning strategy of the present disclosure used both processes to create patterned antigen regions interleaved with non-reactive 'spacer' regions. Spacers were created by biotin saturation of streptavidin to "block" subsequent immobilization of biotinylated capture proteins.

Quantitatively, the different behaviors used to fabricate the barcode pattern can be described by considering the competition between electromigration and biotin-streptavidin binding that yields either protein migration along the axis (no binding) or immobilization of biotinylated protein in the gel (binding). To describe the behavioral regimes, a Damkohler number (Da) was formulated comparing the reaction time scale ($t_r=k_{on}^{-1}*b_m^{-1}$) to the electromigration time scale ($t_i=L/u_i$, where $u_i=\mu E$) through the relationship $Da=t_i/t_r=Lk_{on}b_m/\mu E$. Here, $k_{on}$ was the association constant, $b_m$ was the concentration of the available capture sites, L was the characteristic length of the capture region, $u_i$ was the speed of the electromigration, µ was the electrophoretic mobility, and E was the electric field.

When Da<1, reaction was slow compared to electromigration and binding was limited by the reaction speed. In this regime, electromigration of proteins was fast (compared to the binding kinetics) through the streptavidin-PA gel such that biotinylated capture proteins did not spend enough time in the neighbourhood of a streptavidin binding site to become immobilized. Alternately, there may be few streptavidin binding sites available ($b_m \rightarrow 0$) such that biotinylated proteins moved along the axis of the channel without becoming immobilized.

Alternatively, where Da>10, the binding reaction was mass transport limited such that biotin-streptavidin reaction kinetics were faster than the electromigration timescale. Thus, the immobilization efficiency was high in mass transport limited operation. For barcode patterning, operation in the mass transport limited regime resulted in successful immobilization of biotinylated protein to the streptavidin-PA gel. The range of 1<Da<10 was expected to be a transition region between the two regimes.

Patterning of Alternating Capture Protein and Spacer Regions

Barcode patterning in a single inlet/single outlet channel used a sequence of patterning/blocking steps to create the spacer regions and the capture protein regions (FIGS. 2(B) and 2(C)). First, to create the spacer regions, the streptavidin-PA gel sites were saturated with high concentrations of free biotin ($b_m \rightarrow 0$) (e.g., biotin that was non bound to a capture member). These regions thus allowed subsequent electromigration of biotinylated capture proteins through the non-reactive gel and down the channel axis. Second, to pattern regions of capture reagent, the device was operated under conditions in which streptavidin was in excess in the PA gel. Biotinylated proteins were electrophoresed into the channel and immobilized at open streptavidin sites in the gel matrix. The biotinylated proteins non-covalently bound to streptavidin sites in an ordered fashion, starting at the reservoir of origin. Electromigration of biotinylated protein along the channel—without immobilization—was possible when the local streptavidin became saturated or when transport was faster than the binding reaction. By alternating spacer and capture protein patterning, a single inlet/single outlet microchannel supported fabrication of a multiplexed barcode assay comprised of spacer regions between different capture antigens.

To assess the patterning strategy, a barcode assay was fabricated that included spacer regions and biotinylated c100p as the capture protein. FIG. 4(A) shows a patterning time course. Prior to introduction of biotinylated c100p capture protein, a small spacer region was fabricated at the channel inlet, identified as region (i) in FIG. 4(A). After patterning of the spacer region, the polarity of the electric potential was reversed and unbound biotin was electrophoresed out of the channel. After reservoir flushing via aspiration, patterning of capture protein commenced with biotinylated c100p antigen electromigrating into the channel. As observed in FIG. 4(A), biotinylated c100p migrated through the spacer region (i) with negligible immobilization of c100p. As c100p entered the unblocked streptavidin-PA gel region (iii), the biotinylated c100p capture protein became immobilized and started forming region (ii). Fabrication conditions were estimated to be Da~60.

As shown in FIG. 4(B), as the capture protein concentration front migrated along the channel axis; a self-sharpening behaviour at the interface between regions (ii) and (iii) with enrichment in the protein concentration in region (ii) was observed. The self-sharpening behavior was attributed to a favorable adsorption dynamics with fast capture kinetics. Saturating the available sites, immobilized protein concentration was expected to be enriched by a factor of n, where n is the ratio of the concentration of the available capture sites to the concentration of the biotinylated proteins to be immobilized in the gel. The 3.4±0.2 fold increase in the fluorescence signal in region (ii) agreed with the enrichment factor for the given 5 µM biotinylated c100p protein and 4 µM streptavidin (i.e., providing 16 µM biotin capture site, 16/5=3.2). The electrophoretic velocity $u_i$ was $u_i=\mu_i E$ where $\mu_i$ was the electrophoretic mobility of the protein sample in a given gel medium and E was the applied electric field. From conservation of the mass, the velocity of the moving boundary in region (ii) $v_i$ was expected to decrease with the order of the enhancement factor n, resulting $v_i=u_i/n=\mu_i E/n$. From FIG. 4(B) the reduction in the velocity was found to be 3.5±0.5 which was in agreement with the increase observed in the fluorescence signal (3.4±0.2).

Figure 5:
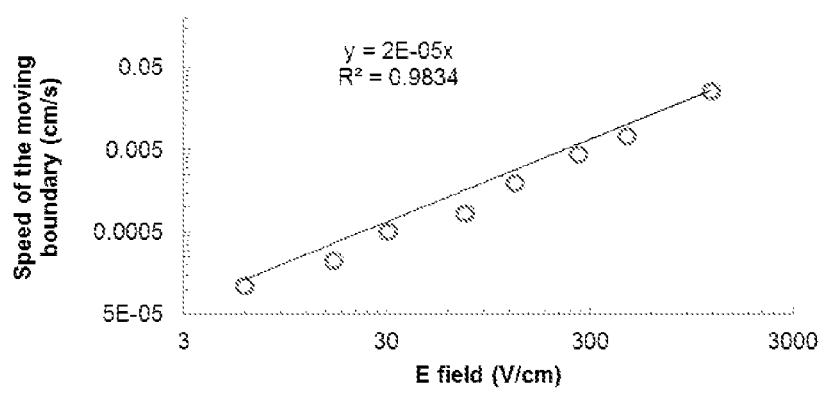
FIG. 5 shows a graph of the speed of the moving boundary, which increased linearly with the electric field ($v_i = \mu_i E/n$), where the slope $2.2 \times 10^{-5}$ cm$^2$V$^{-1}$ s$^{-1}$ was the ratio of mobility ($\mu_i$) to the enhancement factor (n). At 30V/cm, patterning of a 800 µm long zone took 160 seconds, whereas at 1180 V/cm, patterning took about 3 seconds.

With continued electromigration of biotinylated c100p capture protein from the reservoir, the boundary of the immobilized capture protein region penetrated further along the microchannel axis, yielding a longer axial extent of immobilized capture protein, $\Delta x_i$ (FIG. 4(A)). This distance $\Delta x_i$ depended on the velocity of the expanding boundary $v_i$, and the duration of the injection, $\Delta t_i$ ($\Delta x_i=v_i\Delta t_i=\mu_i E\Delta t_i/n$) and was optimized for each capture protein by controlling the duration of the loading process or applied electric field. For instance, as shown in FIG. 4(A) at 10 V drive (40V/cm), patterning of an 800 µm long region with c100p antigen loaded at 5 µM was achieved within 140 s. For comparison, the same patterned length was achieved in 3 s at 300V (1200V/cm) drive (see FIG. 4(C) and FIG. 5). Protein patterning required 100 pg of biotinylated c100p protein. After patterning the capture protein region, unbound biotinylated c100p antigen was electrophoresed out of the microchannel by applying a reverse polarity electric field. The process was repeated to create a barcode pattern of capture protein and spacer regions.

The Role of Da in Control of Interfaces Between Barcode Regions

Experiments were performed to study the interplay of electromigration and binding reactions—the final patterned capture protein distributions were assessed across a range of Da numbers (FIGS. 4(C) and 4(D)). The sharpness of the patterned front was examined using the width (4a) of first derivative of the axial concentration distribution (FIG. 4(C)). To span the range of Da numbers (from 183 to 2.6), the applied electric field was varied (E=17 to 1200 V/cm), with all other conditions held constant, assuming L=35 µm, $b_m$=16 and $k_{on}$=3×10$^6$ M$^{-1}$ s$^{-1}$. A Da number associated dependence of both the axial and the transverse antigen concentration distributions was observed, as described below.

In the Da>10 regime (E<140V/cm), where reaction kinetics were expected to be fast compared to electromigration, a sharp boundary at the leading edge of the concentration front was observed. Experiments were performed to test the 10>Da>1 transition regime (1200 V/cm>E>140V/cm) where the transport time became comparable to the reaction time. In this transition regime, the biotinylated c100p concentration front exhibited a broader axial concentration distribution than the sharp fronts observed in the Da>10 region. In the Da ~2.6 regime, under the highest electric field loading condition (1200 V/cm), the width of the concentration front was expanded to almost 0.3 mm. With Da slightly larger than 1, the reaction was anticipated to exhibit mass transport limited behavior. Stated another way, for this system, the time scale of the capture reaction ($t_r=k_{on}^{-1}*b_m^{-1}$) was 0.02 s. Under a 50V/cm loading condition (Da 60), a biotinylated c100p molecule proceeded only 0.6 µm into the streptavidin-PA gel before being immobilized whereas at 1200V/cm (Da~2.6) the same molecule migrated 15 µm before immobilization. A width that remained constant (34±2 µm) for Da>10 (E<140V/cm) and increased with decreasing Da number was observed.

In addition to (axially) broader leading edge behavior, a transverse parabolic profile was observed with decreasing Da (i.e., increasing electric field) as shown in FIG. 4(C). While microfluidic systems dissipated Joule heating effectively due to favorable surface area to volume ratios, at very high electric fields heat generation can raise the temperature and generate temperature gradients in the channel.

Inclusion of a 30 to 60 s incubation step (E=0 V/cm, no electromigration) during patterning of region (ii) enhanced biotinylated capture protein immobilization in the streptavidin-PA gel at the leading edge of the concentration front. During the incubation period, unbound biotinylated c100p in region (ii) diffused into region (iii), leading to a slow but sharp expansion of the interface according to a competition between reaction and diffusion. For high diffusivity species including biotin and biotinylated c100p (2 kDa), expansion of the leading edge resulted in extension of the patterned region by ~50 µm after 1 min of incubation.

Validating the Selectivity of the Barcode Immunoassay

Having established the capacity to pattern capture proteins and spacer regions in a single channel with just one inlet and outlet, experiments were performed to develop a barcode assay for human serum antibodies against three HCV antigens (core, c100p and NS3).

To yield a selective assay, each immobilized antigen region specifically interacted with a corresponding antibody target with minimal cross-reactivity or nonspecific interaction with off-target antibodies. To understand the potential for cross-reactivity, two specific aspects of the assay were characterized: the cross-reactivity of the reagents and the cross-reactivity inherent to the barcode assay format.

Figure 6:
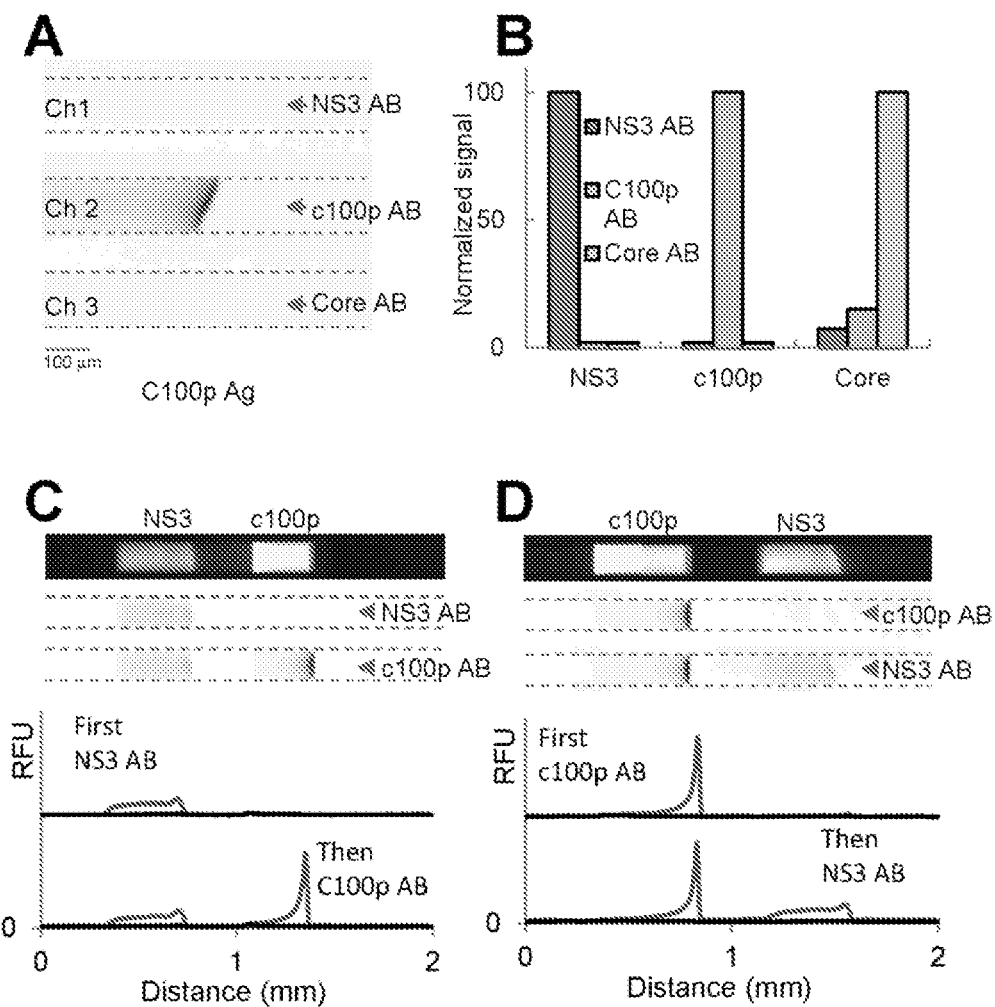
FIG. 6 shows cross-reactivity and immobilized antigen purity according to embodiments of the present disclosure.

First, experiments were performed to determine the possibility of nonspecific interactions between the reagents. To do this, each capture protein was immobilized in one of three different channels. Each immobilized capture protein was challenged by each of the three antibody targets individually (9 total channels). FIG. 6(A) shows the antibody signal in three channels, each housing a region of immobilized c100p capture protein. One of the target antibodies was electrophoretically loaded into each channel: 1 µg/ml NS3, C100p, Core (AF568).

As shown in FIG. 6(A), negligible signal from off-target antibodies (NS3, core) was observed, but significant signal from the C100p antibody was observed (SNR=70). (This data showed non-uniform antibody immobilization across the target binding region, discussed in the next section.) Similarly, all three antibodies were loaded against channels individually patterned with NS3 and core capture proteins. FIG. 6(B) showed c100p and NS3 capture proteins with negligible off-target cross-reactivity. Core antigen, however, exhibited some nonspecific capture of c100p (SNR=38) and NS3 (SNR=12) antibodies along with the expected core antibody capture (SNR>200). In certain embodiments, under specific buffer conditions, Core antigen exhibited nonspecific interactions with generic human IgG's from the Fcγ fragment.

Second, experiments were performed to determine cross-reactivity inherent to the single channel barcode assay format; namely, the possibility of patterning of more than one capture protein in each region during device fabrication. Based on the patterning principle, channel regions closest to the inlet were patterned with capture protein first, such that antigen used for patterning down-stream regions does not "co-pattern" the already patterned near-inlet regions. In other words, new capture proteins may electromigrate through all previously patterned regions without becoming immobilized. Specificity in patterning may facilitate the patterning of multiple capture proteins in a single inlet/single outlet channel.

To test patterning specificity, NS3 was immobilized first, and then C100p antigens were immobilized in a single channel (FIG. 6(C)). As such, NS3 was located closest to the channel inlet. After patterning of this multiplexed capture protein assay, NS3 Ab was loaded into the channel from the right. NS3 antibody capture (SNR=30) was observed co-localized with NS3 suggesting that all streptavidin binding sites in the C100p region were saturated with either biotinylated C100p or biotin prior to the start of the assay. Given this observation, c100p antibodies were subsequently loaded to the channel to confirm the presence and location of the C100p region. In this C100p test, antibody capture was observed in the c100p region only (SNR=145).

To further investigate the potential for unwanted co-patterning of capture proteins, the assay was repeated (in a new channel) but reversed the order of immobilization of the capture proteins as well as the order of the antibody load. When c100p antibodies were loaded, the c100p antibodies passed through the NS3 region with negligible interaction, and the c100p antibodies bound in the C100p region (SNR=172). Similarly, no off-target binding behavior for the NS3 antibodies was observed, with capture only localized to the NS3 region (SNR=41). Thus, no nonspecific capture was observed, allowing the patterning of single, unique capture proteins in spatially distinct regions of a single straight microchannel.

Different antibody signals were observed for the NS3 and c100p readouts (FIGS. 6(C) and 6(D)). Such differences in readout behavior may arise from a variety of sources. Specific differences may arise from: (1) Residual free biotin from the biotinylation reaction that may reduce the antigen immobilization efficiency. If unbound biotin was in the solution, some sites may be filled by the free biotin. This effect may become pronounced in cases where the protein mobility was low compared to the biotin mobility. A lower immobilized antigen concentration may lead to lower and more dispersed antibody capture in a given antigen band; (2) Intrinsic differences in binding affinity between different antibody antigen pairs may also contribute to lower or dispersed antibody signal. Rather than capturing the antibody mostly at the region entrance (e.g., c100p case), a lower affinity may lead to a disperse capture spread over the entire capture region (e.g., NS3 case); (3) Even if affinity is similar for antigen antibody pairs, biotin or fluorophore conjugation may block the active antigen epitopes leading to a reduced apparent affinity; (4) c100p is a 2 kDa peptide whereas molecular weight of NS3 is 45 kDa. The relatively large size of NS3 may trigger steric hindrance during immobilization in the streptavidin sites or during the target antibody-antigen interaction. Nevertheless, for all antigen antibody pairs tested, target antibody detection was possible across a clinically relevant range (ng/ml-µg/ml).

Maximizing Antibody Detection with the Barcode Immunoassay

Antibody detection may depend, in part, on the amount of antibody delivered to the capture protein region and the capture efficiency of that region. On one hand, increasing the applied electric field strength may increase the total mass of target antibody probed by the capture protein over a set duration. On the other hand, depending on the Da regime, increasing the electric field may diminish capture efficiencies. To assess this interplay, antibody detection over a set 10 minute long detection step for a range of electric field conditions was characterized. As with the patterning protocol, the detection of antibodies in the barcode immunoassay depended on both transport and reaction, now reaction in the form of antigen-antibody binding.

Figure 7:
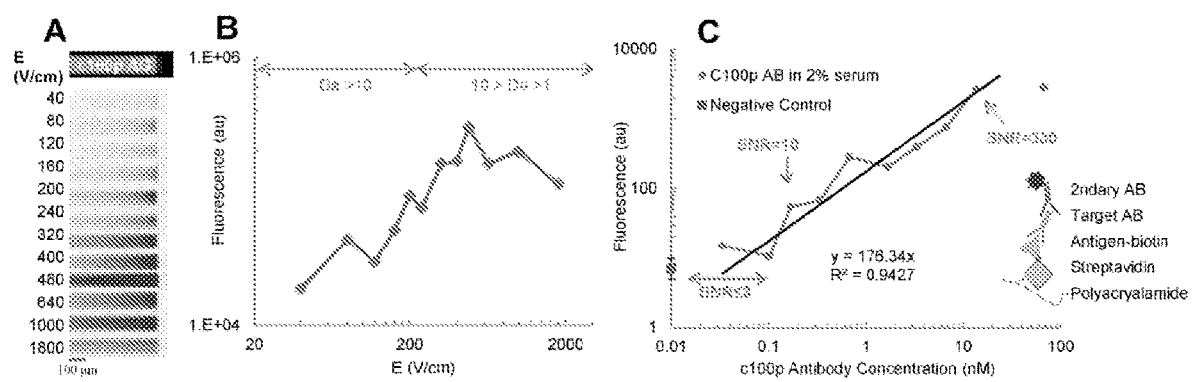
FIG. 7 shows optimization of the barcode assay antibody detection conditions according to embodiments of the present disclosure.
Figure 8:
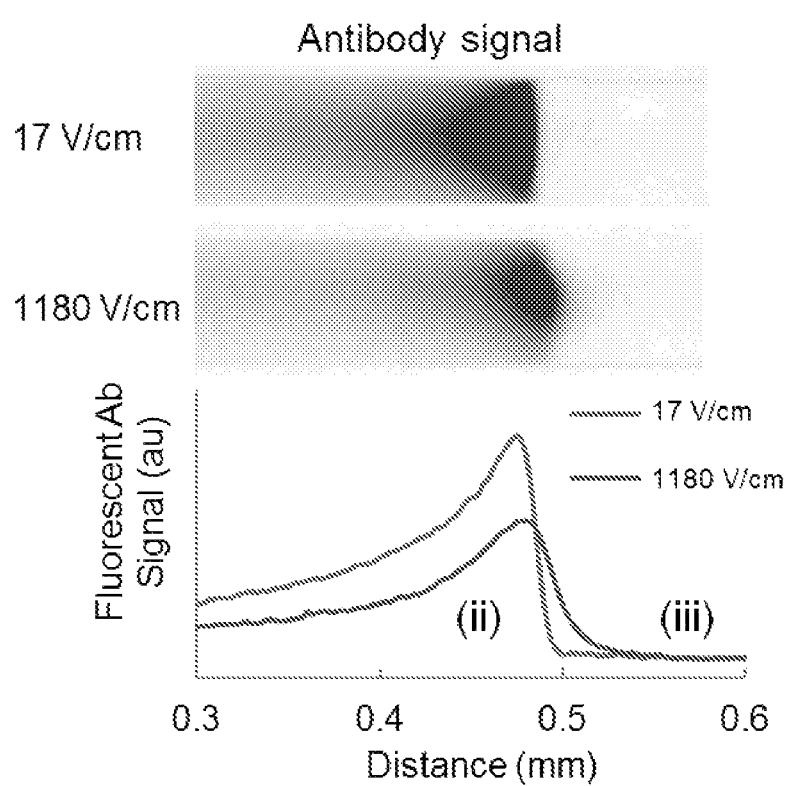
FIG. 8 shows the effect of immobilization conditions over antibody capture according to embodiments of the present disclosure. Channels in which antigens were immobilized at different electric fields (17V/cm and 1180V/cm) were tested with loading of c100p (AF-568) antibodies from the right direction.
Figure 9:
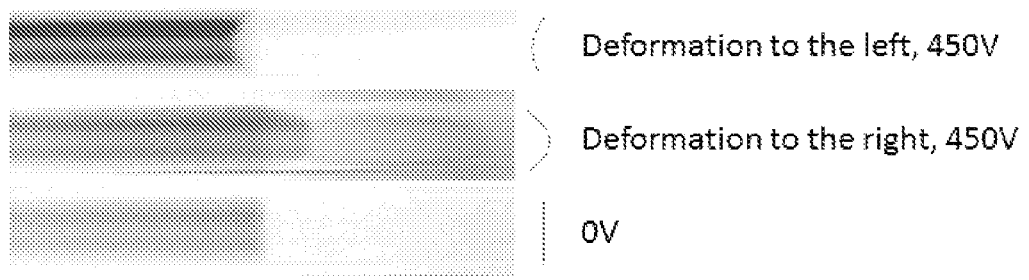
FIG. 9 shows images of gel deformation under high electric field. AF-568 labeled c100p antibodies were loaded against c100p antigen band at 450V (1800V/cm). In the first few minutes of the loading, deformation was along the loading direction (convex to the left). With the loss of the buffer in the left well, deformation changed direction towards the right. Loss of the buffer in the left well can be attributed to the electroosmotic pumping of the fluid from the left well to the right well through the deformations within the gel matrix or gel-glass wall interface after the application of high voltage. When the applied voltage was turned off, the gel profile regained its original form.

FIG. 7(A) shows antibody detection signal after 10 minute loading of fluorescently labeled c100p antibody (AF-568 labeled 1 µg/ml 6.5 nM) across a range of applied electric fields. Here, c100p capture protein was immobilized in 12 different channels (1 uA, 9V). Antibody signal increased with increasing electric field until 500 V/cm (125V, Da ~6.7), as shown in FIG. 7(B). In this regime, reaction was mass transport limited such that signal was restricted by the rate of antibody delivered to the antigen sites. Stated another way, nearly all antibody mass delivered to the binding sites was anticipated to be captured. For our estimated parameters (L=100 µm, $b_m$=16 µM, $k_{on}$=2×10$^5$M$^1$ s$^1$, $\mu_i$=1×10$^{-5}$ cm$^2$V$^{-1}$ s$^{-1}$) the Da number remained larger than 10 when the E<320V/cm. With E>320V/cm the operational regime spanned 10>Da>1, such that while the antibody delivery increased, the decline in the capture efficiency limited the total antibody capture. In this regime, reaction time became comparable to the time spent in the capture region. As an additional consideration, when the loading time exceeded ~10 min, antibodies captured in the early stage of the detection stage may disassociate ($k_{off}$~10$^{-3}$-10$^{-4}$ s$^{-1}$) from the capture protein and electromigrate down the channel under high field. However, even at 1800 V/cm at 450V drive, appreciable signal (SNR>1000) was obtained. At this high voltage, gel deformation was observed (FIG. 9). In summary, even at high fields, beyond the operation limit of the device, highly efficient antibody capture was observed.

The efficient antibody capture observed in FIG. 7(B) was due to utilization of directed electromigration of antibody target through a 3D gel matrix that included a high density of antigen capture sites. First, the gel matrix supported 2-3 orders of magnitude more capture reagent per given length of a microchannel section compared to channel walls functionalized with capture protein. Second, diffusion distances between antibody target and antigens immobilized in the 3D gel were significantly reduced, compared to channel wall functionalization approaches. Highly efficient antibody capture was validated by the non-uniform antibody signal across the target binding region shown in FIGS. 6(A), 6(C) and 7(A). Delivered from the right direction, antibodies entering to the antigen regions immediately were captured at the beginning of antigen regions leading to a signal peak towards the edge of the antigen regions.

Barcode Immunoassay Validated for Serological Analyses

As shown in FIG. 7(C), the microfluidic barcode immunoassay was used for serological detection of human antibodies against a single HCV antigen, c100p. To test the microfluidic assay on a complex sample, unlabeled human antibodies against HCV-c100p were added into 2% healthy human serum (diluted 50-fold in TG buffer). For example, 1%-2% was the typical serum dilution range used in Western blot and HCV-RIBA. As shown in FIG. 7(C), a sandwich detection format was used, with fluorescently labelled (AF-568) anti-human goat antibody as the readout. Total assay runtime was 30 minutes with triplicate assays performed. All assay steps were performed electrophoretically (see Table 2). FIG. 7(C) shows the dose response curve from the clinically relevant titers (5 ng/ml-10 µg/ml in 2% human serum) analysed. Detectable signal was obtained down to 5 ng/ml (33 pM). The lower limit of detection (LOD) was determined to be 25 ng/ml (165 pM) where SNR=10. Spanning an almost 3 orders of magnitude concentration range, the linear dynamic range of the assay was 33 pM-13.5 nM (5 ng/ml-2 µg/ml). For context, LOD for the c100p antibody using an HCV-RIBA assay was reported to be 25 ng/ml. Incorporation of enzymatic amplification to the microfluidic barcode assay may facilitate a further decrease in the LOD. The microfluidic barcode assay used a 10 min antibody detection step.

Figure 10:
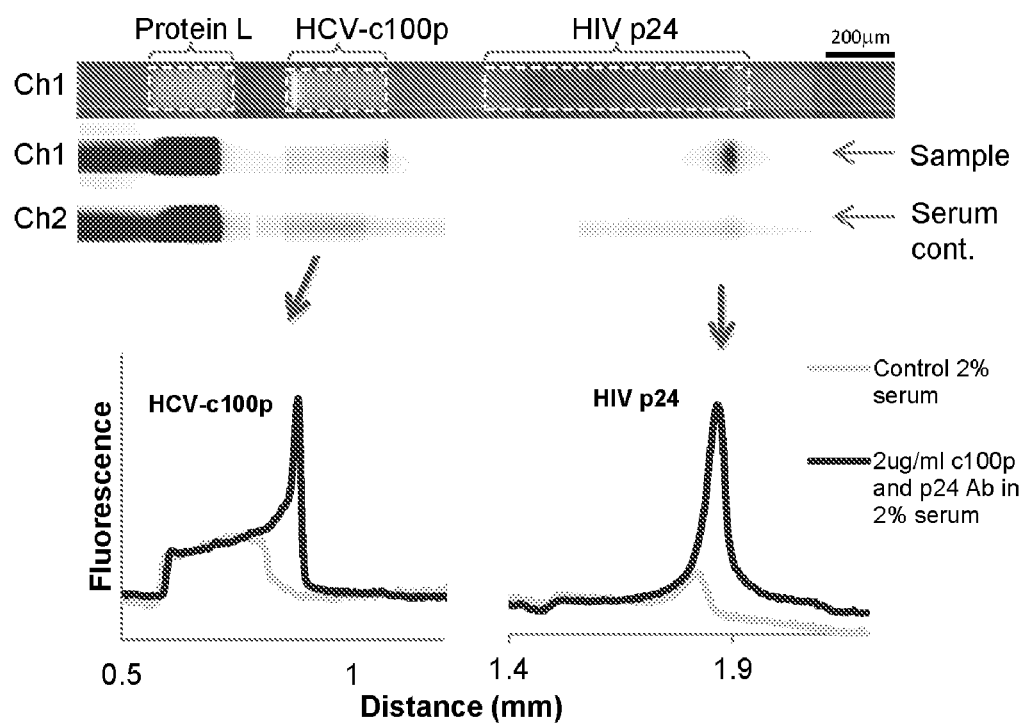
FIG. 10 shows a multiplexed microfluidic barcode assay for detection of serum antibodies to HIV and HCV according to embodiments of the present disclosure.

Experiments were performed to develop a multiplexed serological assay for HIV and HCV antibodies. Three antigens and interleaving biotin spacers were patterned: protein L (loading control), HCV-c100p and HIV-p24. The protein L region was included to capture serum IgG and yield signal in cases were serum was successfully loaded. As a model system, 2 µg/ml of HCV-c100p (human) and HIV-p24 (mouse) antibodies were added into 2% human serum diluted in TG buffer. Detection antibody cocktail consisted of AF-568 labelled anti-human and anti-mouse IgG. FIG. 10 shows fluorescence micrographs and corresponding fluorescence intensity profiles of two microchannels, labelled Ch1 and Ch2. Channel 1 assayed HCV-HIV antibody cocktail in 2% serum and channel 2 assayed 2% human serum without target antibodies. In channel 1, the c100p region captured HCV-c100p antibodies and HIV-p24 region captured HIV-p24 antibodies. In both channels, the protein L region successfully detected IgG indicating successful serum loading.

CONCLUSIONS

As a basis for rapid, low-resource confirmatory diagnostics, a simple single straight microchannel housing a multiplexed heterogeneous immunoassay format is provided. Assay design, assay fabrication, and assay operational specifications were discussed above. In certain embodiments, the device includes a 'single inlet, single outlet' microchannel to simplify device operation. In certain embodiments, a fully electrophoretic approach was used, with no pumps or valves used to provide bulk fluid flow.

In certain embodiments, for assay fabrication, a new electrophoretic patterning strategy that used microchannel-filling streptavidin-decorated polyacrylamide gels as immobilization scaffolds is provided. Sequential introduction of either free biotin or biotinylated capture proteins yields a "spacer-capture region-spacer" barcode pattern in the channel. Experiments were performed to determine the patterning process across a wide range of Da numbers. Antibody detection was characterized by detecting an antigen-antibody interaction across a range of Da numbers.

In assay operational specifications, the format was electronic (single electrode pair) with electrophoresis conducted at low applied voltages. Low voltage and low power operation facilitates the production of a portable device that does not depend on high voltage power supplies, pumps, syringes, or valves, thus making the device appropriate for near-patient operation. The multiplexed microfluidic barcode assay was validated for detection of immunoglobulin specific for HCV-c100p, HCV-NS3 and HIV-I p24 antigens. The assay was completed in 30 minutes with an analytical sensitivity comparable to the 6+ hour RIBA 3.0 assay. Performance advances were attributable to use of directed electromigration through functionalized 3D polyacrylamide gels.

In certain embodiments, the single channel microfluidic barcode assay may be integrated with standalone electronics to provide an automated and portable confirmatory diagnostic platform. Embodiments of the microfluidic device have a short assay run time and high sensitivity. In certain embodiments, a massively multiplexed version of the platform may facilitate screens used at blood banks and in pharmaceutical applications where high throughput (rapid and multiplexed) readouts are desired.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An assay device comprising:
    a microchannel comprising a polymeric medium, wherein the polymeric medium comprises:
    a first analyte detection domain, wherein the first analyte detection domain comprises a first immobilized capture member that specifically binds to a first analyte;
    a second analyte detection domain, wherein the second analyte domain comprises a second immobilized capture member that specifically binds to a second analyte; and
    a spacer domain disposed between the first analyte detection domain and the second analyte detection domain, wherein the spacer domain comprises a first member of a specific binding member pair bound to a second member of the specific binding member pair, wherein the second member of the specific binding member pair is not bound to a capture member, wherein the first member and the second member do not bind to the first analyte or the second analyte,
    wherein the first member of the specific member binding pair is coupled to the polymeric medium throughout the entire polymeric medium,
    wherein the first immobilized capture member and the second immobilized capture member are immobilized to the polymeric medium through the first member.

2. The assay device according to claim 1, wherein the polymeric medium comprises a polymeric gel.

3. The assay device according to claim 1, wherein the first immobilized capture member is bound to the polymeric medium in the first analyte detection domain.

4. The assay device according to claim 3, wherein the first immobilized capture member is non-covalent bound to the polymeric medium in the first analyte detection domain via a specific binding member pair.

5. The assay device according to claim 4, wherein the specific binding member pair comprises biotin and streptavidin.

6. The assay device according to claim 5, wherein the first immobilized capture member comprises streptavidin bound to the polymeric medium and biotin bound to a ligand of the first analyte.

7. The assay device according to claim 1, wherein the second immobilized capture member is bound to the polymeric medium in the second analyte detection domain.

8. The assay device according to claim 7, wherein the second immobilized capture member is non-covalently bound to the polymeric medium in the second analyte detection domain via a specific binding member pair.

9. The assay device according to claim 8, wherein the specific binding member pair comprises biotin and streptavidin.

10. The assay device according to claim 9, wherein the second immobilized capture member comprises streptavidin bound to the polymeric medium and biotin bound to a ligand of the second analyte.

11. A method of determining whether an analyte is present in a sample, the method comprising:
    introducing a sample into a microchannel comprising a polymeric medium, wherein the polymeric medium comprises:
        a first analyte domain comprising a first immobilized capture member that specifically binds to a first analyte;
        a second analyte domain comprising a second immobilized capture member that specifically binds to a second analyte; and
        a spacer domain disposed between the first analyte detection domain and the second analyte detection domain, wherein the spacer domain comprises a first member of a specific binding member pair bound to a second member of the specific binding member pair, wherein the second member of the specific binding member pair is not bound to a capture member, wherein the first member and the second member do not bind to the first analyte or the second analyte,
        wherein the first member of the specific member binding pair is coupled to the polymeric medium throughout the entire polymeric medium,
        wherein the first immobilized capture member and the second immobilized capture member are immobilized to the polymeric medium through the first member;
    applying a directional electric field to the microchannel in a manner sufficient to move components through the polymeric medium; and
    obtaining a signal from the first analyte detection domain and the second analyte detection domain to determine whether the first analyte and the second analyte are present in the sample.

12. The method according to claim 11, comprising labeling the sample prior to introducing the sample into the microchannel.

13. The method according to claim 11, comprising introducing a label into the elongated flow path after the sample is introduced into the microchannel.

14. The method according to claim 13, wherein the label is a detectable label.

15. The method according to claim 14, wherein the detectable label comprises a fluorescent moiety.

16. The method according to claim 11, wherein the analyte is selected from a protein, a peptide, an antibody, a diabody, a Fab fragment, a DNA binding protein, an RNA binding protein, a phosphorylated protein, a peptide aptamer, and an epitope.

17. The method according to claim 11, wherein the sample comprises urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, or a sample obtained from laser capture microdissection (LCM).

18. A system for assaying a fluid sample for the presence of two or more analytes, the system comprising:
(a) an assay device according to claim 1; and
(b) a detector.

19. The system according to claim 18, further comprising components configured to direct a fluid through the assay device.

20. A kit comprising:
(a) an assay device according to claim 1; and
(b) a packaging configured to contain the assay device.

21. A method of producing an assay device, the method comprising:
producing a precursor polymeric medium in a microchannel, wherein the precursor polymeric medium comprises a first member of a specific binding pair coupled to the polymeric medium throughout the entire polymeric medium;
introducing into the microchannel a defined amount of a first capture member bound to a second member of the specific binding pair in a manner sufficient to produce a first analyte detection domain that comprises a first immobilized capture member that specifically binds to a first analyte in the microchannel, wherein the first immobilization capture member is immobilized to the polymeric medium through the first member;
introducing into the microchannel a defined amount of the second member of the specific binding pair in a manner sufficient to produce a spacer domain,
wherein the spacer domain comprises the first member of the specific binding member pair bound to the second member of the specific binding member pair, wherein the second member of the specific binding member pair is not bound to a capture member; and
introducing into the microchannel a defined amount of a second capture member bound to the second member of the specific binding pair in a manner sufficient to produce a second analyte detection domain that comprises a second immobilized capture member that specifically binds to a second analyte in the microchannel, wherein the second immobilization capture member is Immobilized to the polymeric medium through the first member;
wherein the spacer domain is disposed between the first analyte detection domain and the second analyte detection domain, wherein the first member and the second member do not bind to the first analyte or the second analyte
to produce the assay device.

22. The method according to claim 21, wherein introducing the first capture member into the microchannel produces a higher concentration of the immobilized first capture member in the first analyte detection domain as compared to the concentration of the first capture member in the defined amount of the first capture member.

23. The method according to claim 22, wherein introducing the second capture member into the microchannel produces a higher concentration of the immobilized second capture member in the second analyte detection domain as compared to the concentration of the second capture member in the defined amount of the second capture member.

24. The method according to claim 21, further comprising introducing into the microchannel a defined amount of one or more additional capture members in a manner sufficient to produce one or more corresponding analyte detection domains each comprising the corresponding capture member immobilized in the polymeric medium, wherein each of the one or more capture members specifically binds to a specific analyte, wherein each corresponding capture member is immobilized to the polymeric medium through the first member.

25. The system of claim 18, wherein the system comprises an array of two or more of the assay devices.

26. The system of claim 25, wherein the assay devices in the array comprise different capture members.

27. The system of claim 25, wherein the assay devices in the array comprise the same capture members.

28. The assay device according to claim 1, wherein the first analyte detection domain and the second analyte detection domain are arranged in series along a single directional axis, wherein the first analyte detection domain comes before the second analyte detection domain.

29. The assay device according to claim 1, wherein the first member of the specific binding member pair in the spacer region is blocked from binding a second member of the specific binding member pair that is bound to a capture member.

30. The assay device according to claim 1, wherein the microchannel comprises a single inlet and a single outlet.

31. The assay device according to claim 1, wherein the polymeric medium fills an interior volume of the microchannel.

* * * * *

UNITED STATES PATENT AND TRADEMARK OFFICE
CERTIFICATE OF CORRECTION

PATENT NO. : 10,634,673 B2
APPLICATION NO. : 14/440852
DATED : April 28, 2020
INVENTOR(S) : M. Kursad Araz et al.

It is certified that error appears in the above-identified patent and that said Letters Patent is hereby corrected as shown below:

In the Claims

At Column 45, Line 5, the recitation of "the elongated flow path" should read -- the microchannel --.

Signed and Sealed this
Twenty-eighth Day of July, 2020

Andrei Iancu
*Director of the United States Patent and Trademark Office*